United States Patent
Gross et al.

(10) Patent No.: US 6,964,659 B2
(45) Date of Patent: Nov. 15, 2005

(54) THERMAL MODELING FOR REDUCTION OF REFRACTIVE LASER SURGERY TIMES

(75) Inventors: Erik Gross, Palo Alto, CA (US); Kingman Yee, San Jose, CA (US); Jonathan Wong, Santa Clara, CA (US)

(73) Assignee: VISX, Incorporated, Santa Clara, CA (US)

( * ) Notice: Subject to any disclaimer, the term of this patent is extended or adjusted under 35 U.S.C. 154(b) by 161 days.

(21) Appl. No.: 10/447,667

(22) Filed: May 28, 2003

(65) Prior Publication Data

US 2004/0111083 A1 Jun. 10, 2004

Related U.S. Application Data

(60) Provisional application No. 60/431,355, filed on Dec. 6, 2002, and provisional application No. 60/384,621, filed on May 30, 2002.

(51) Int. Cl.[7] ............................................. A61B 18/18
(52) U.S. Cl. ................................ 606/5; 606/4; 606/10; 606/12; 128/898
(58) Field of Search ........................... 606/4–6, 10–12; 128/898

(56) References Cited

U.S. PATENT DOCUMENTS

| | | | |
|---|---|---|---|
| 4,941,093 A | 7/1990 | Marshall et al. | |
| 5,061,342 A | 10/1991 | Jones | |
| 5,137,530 A | * 8/1992 | Sand | 606/5 |
| 5,170,191 A | 12/1992 | Jones | |
| 5,240,553 A | 8/1993 | Jones | |
| 5,294,293 A | 3/1994 | Jones | |
| 5,348,551 A | 9/1994 | Spears et al. | |
| 5,683,379 A | 11/1997 | Hohla | |
| 5,741,245 A | 4/1998 | Cozean et al. | |
| 5,993,441 A | 11/1999 | Muller et al. | |
| 6,059,772 A | 5/2000 | Hsia et al. | |
| 6,080,148 A | 6/2000 | Damasco et al. | |
| 6,099,521 A | 8/2000 | Shaddock | |
| 6,099,522 A | * 8/2000 | Knopp et al. | 606/10 |
| 6,190,377 B1 | * 2/2001 | Kuzdrall | 606/10 |
| 6,482,199 B1 | 11/2002 | Neev | |
| 2002/0035359 A1 | 3/2002 | Yee et al. | |

* cited by examiner

*Primary Examiner*—A. Farah
(74) *Attorney, Agent, or Firm*—Townsend and Townsend & Crew LLP; Mark D. Barrish

(57) ABSTRACT

The present invention provides systems and methods for applying pulsed energy to an eye. In an exemplary embodiment, a firing rate of the pulsed energy varies in correlation with a modeled or estimated thermal response of a tissue of the eye to the pulses of the laser beam during the treatment.

30 Claims, 19 Drawing Sheets

FIG. 11A — Table 342

| Pulse # | 1 | 2 | 3 | 4 | 5 | 6 | 7 | 8 | 9 | 10 | 11 | 12 | 13 | 14 | 15 | 16 | 17 | 18 | ... |
|---|---|---|---|---|---|---|---|---|---|---|---|---|---|---|---|---|---|---|---|
| size (mm) | 2.5 | 2.5 | 3 | 3 | 3.5 | 3.5 | 3.5 | 3.5 | 4 | 4 | 4 | 4 | 4.5 | 4.5 | 4.5 | 5 | 5 | 5 | ... |
| location x | 1.4 | 1 | 0.4 | -0.8 | -2.1 | -1.6 | -1.4 | -0.1 | 0.7 | -0.7 | -1.1 | 1.9 | 0 | -0.7 | -1.6 | 1.4 | -1.6 | 1.4 | ... |
| location y | -2.0 | -1.1 | 0.0 | -1.0 | 2.0 | -0.6 | -1.6 | -0.2 | 0.7 | -1.0 | -1.1 | 2.1 | -0.1 | -0.8 | -0.6 | -2.0 | -0.6 | -2.0 | ... |
| msec | 59 | 59 | 71 | 71 | 83 | 83 | 83 | 83 | 100 | 100 | 100 | 100 | 111 | 111 | 111 | 125 | 125 | 125 | ... |
| time (sec) | 0.08 | 0.12 | 0.19 | 0.26 | 0.34 | 0.43 | 0.51 | 0.59 | 0.69 | 0.79 | 0.89 | 0.99 | 1.10 | 1.21 | 1.33 | 1.45 | 1.58 | 1.70 | ... |

FIG. 11B — Table with selection group 348

| Pulse # | 1 | 2 | 3 | 4 | 5 | 6 | 7 | 8 | 9 | 10 | 11 | 12 | 13 | 14 | 15 | 16 | 17 | 18 | ... |
|---|---|---|---|---|---|---|---|---|---|---|---|---|---|---|---|---|---|---|---|
| size (mm) | 2.5 | 2.5 | 3 | 3 | 3.5 | 3.5 | 3.5 | 3.5 | 4 | 4 | 4 | 4 | 4.5 | 4.5 | 4.5 | 5 | 5 | 5 | ... |
| location x | 1.4 | 1 | 0.4 | -0.8 | -2.1 | -1.6 | -1.4 | -0.1 | 0.7 | -0.7 | -1.1 | 1.9 | 0 | -0.7 | -1.6 | 1.4 | -1.6 | 1.4 | ... |
| location y | -2.0 | -1.1 | 0.0 | -1.0 | 2.0 | -0.6 | -1.6 | -0.2 | 0.7 | -1.0 | -1.1 | 2.1 | -0.1 | -0.8 | -0.6 | -2.0 | -0.6 | -2.0 | ... |
| msec | 50 | 50 | 60 | 60 | 85 | 85 | 85 | 85 | 85 | 85 | 85 | 85 | 96 | 96 | 96 | 102 | 102 | 102 | ... |
| time (sec) | 0.05 | 0.10 | 0.16 | 0.22 | 0.29 | 0.35 | 0.42 | 0.48 | 0.57 | 0.65 | 0.74 | 0.82 | 0.92 | 1.01 | 1.11 | 1.31 | 1.31 | 1.41 | ... |
| Point 1 | ▓ | ▓ | ▓ | ▓ |   |   |   |   |   |   |   |   |   |   |   | ▓ | ▓ | ▓ | ... |
| Point 2 |   |   |   | ▓ | ▓ | ▓ |   |   |   |   |   |   |   |   |   | ▓ | ▓ | ▓ | ... |
| Point 3 |   |   |   |   | ▓ | ▓ | ▓ | ▓ | ▓ |   |   |   |   |   |   | ▓ | ▓ | ▓ | ... |
| Point 4 |   |   |   |   |   |   |   | ▓ | ▓ | ▓ | ▓ | ▓ |   |   |   | ▓ | ▓ | ▓ | ... |
| Point 5 |   |   |   |   |   |   |   |   |   |   |   | ▓ | ▓ | ▓ | ▓ | ▓ | ▓ | ▓ | ... |

FIG. 11C — Table 344

| Pulse # | 1 | 2 | 3 | 4 | 5 | 6 | 7 | 8 | 9 | 10 | 11 | 12 | 13 | 14 | 15 | 16 | 17 | 18 | ... |
|---|---|---|---|---|---|---|---|---|---|---|---|---|---|---|---|---|---|---|---|
| size (mm) | 2.5 | 2.5 | 3 | 3 | 3.5 | 3.5 | 3.5 | 3.5 | 4 | 4 | 4 | 4 | 4.5 | 4.5 | 4.5 | 5 | 5 | 5 | ... |
| location x | 1.4 | 1 | 0.4 | -0.8 | -2.1 | -1.6 | -1.4 | -0.1 | 0.7 | -0.7 | -1.1 | 1.8 | 0 | -0.7 | -1.6 | 1.4 | -1.6 | 1.4 | ... |
| location y | -2.0 | -1.1 | 0.0 | -1.0 | 2.0 | -0.6 | -1.6 | -0.2 | 0.7 | -1.0 | -1.1 | 2.1 | -0.1 | -0.8 | -0.6 | -2.0 | -0.6 | -2.0 | ... |
| msec | 50 | 50 | 60 | 60 | 85 | 85 | 85 | 85 | 85 | 85 | 85 | 85 | 96 | 96 | 96 | 102 | 102 | 102 | ... |
| time (sec) | 0.05 | 0.10 | 0.16 | 0.22 | 0.28 | 0.35 | 0.42 | 0.48 | 0.57 | 0.65 | 0.74 | 0.82 | 0.92 | 1.01 | 1.11 | 1.21 | 1.31 | 1.41 | ... |

Effect of multiple iterations

- Each pass trims a few milliseconds from eligible pulses

- Process completes when no more milliseconds can be trimmed from any pulse.

$$\text{Max\_rep\_rate} = \frac{10^\circ C}{(0.0533r^2 + 0.407r)}$$

| Spot Diameter (mm) | Steady State Rate (Hz) | Steady State Period (Hz) | Practical Rate (Hz) |
|---|---|---|---|
| 6.5 | 6 | 0.167 | 6 |
| 6.0 | 6 | 0.167 | 6 |
| 5.5 | 7 | 0.143 | 7 |
| 5.0 | 8 | 0.125 | 8 |
| 4.5 | 9 | 0.111 | 9 |
| 4.0 | 10 | 0.100 | 10 |
| 3.5 | 12 | 0.083 | 12 |
| 3.0 | 14 | 0.071 | 14 |
| 2.5 | 17 | 0.059 | 17 |
| 2.0 | 22 | 0.045 | 20 |
| 1.5 | 30 | 0.033 | 20+ |
| 1.0 | 46 | 0.022 | 20+ |
| 0.65 | 73 | 0.014 | 20+ |

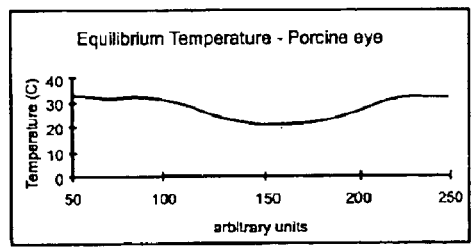

FIG. 13A

A horizontal cross section of the temperature.
Note the temperature reading is 4C low, making the
bath temperature to be about 37C.

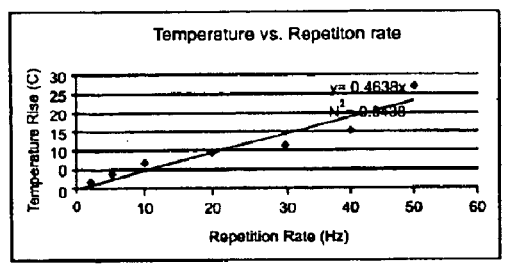

FIG. 13B

Temperature rise versus repetion rate
for a 2mm stationary spot.

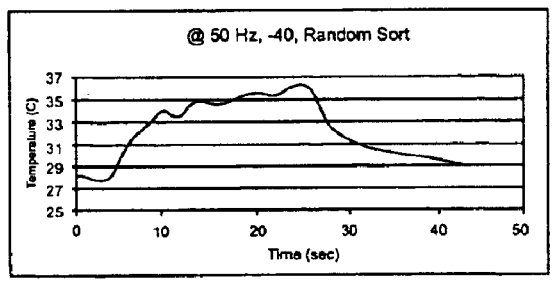

FIG. 13C

Temperature of a -4 D PRK on a
porcine eye. The scan rate was 50 Hz with a spot
size of 2mm. The total rise in temperature was
approx. 35.5-27.9=7.6C.

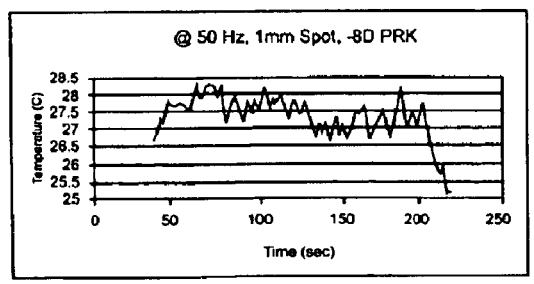

FIG. 13D

Temperature of a -8 D PRK on a
porcine eye. The scan rate was 50 Hz with a spot
size of 1mm. The total rise in temperature was
approx. 24.3-21.3=2C.

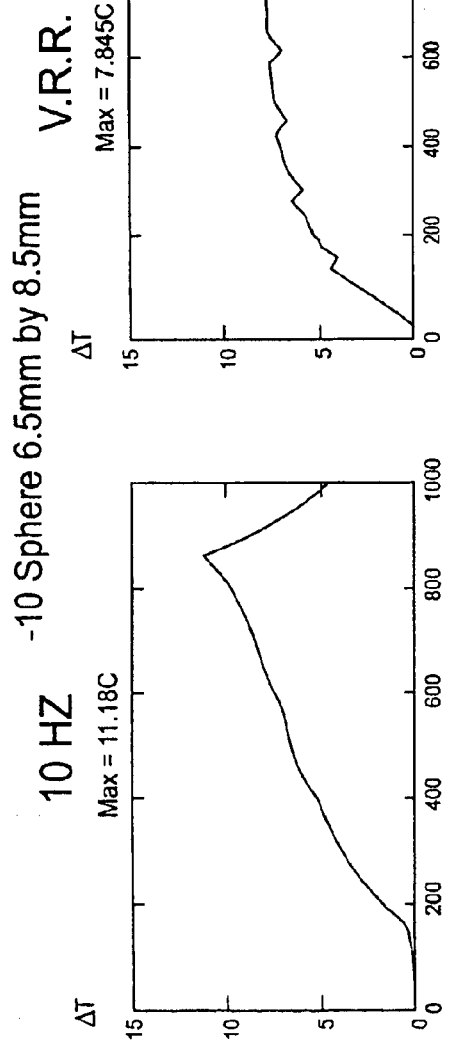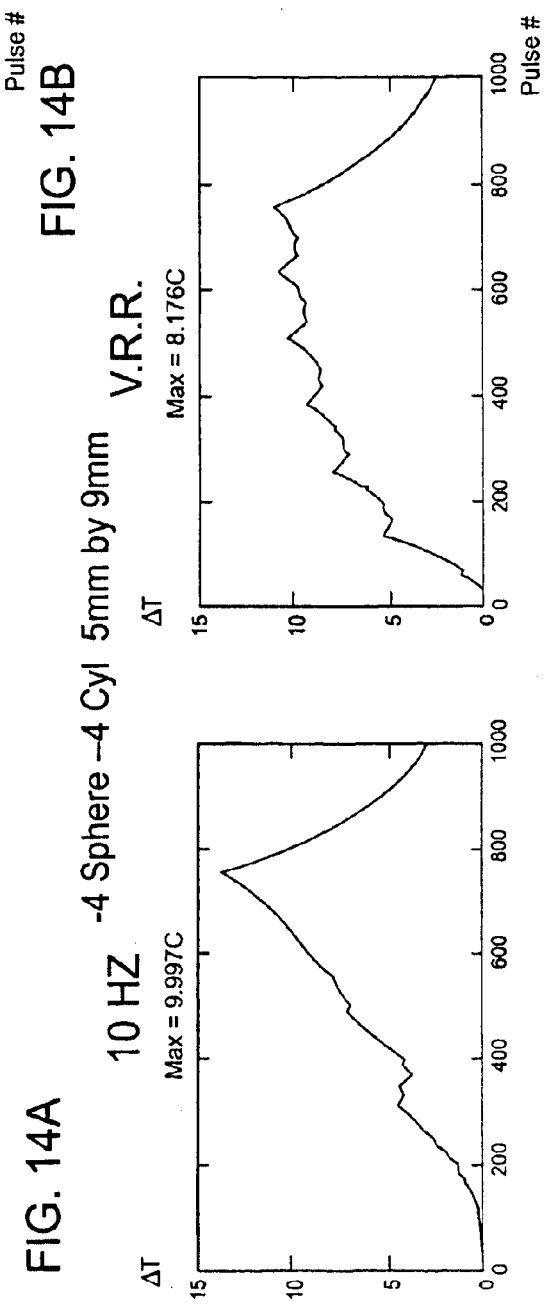

THERMAL MODELING FOR REDUCTION OF REFRACTIVE LASER SURGERY TIMES

CROSS-REFERENCES TO RELATED APPLICATIONS

The present application is a non-provisional U.S. patent application which claims priority from provisional U.S. Patent Application No. 60/431,355 filed Dec. 6, 2002, which is related to U.S. Provisional Patent Application No. 60/384,621 filed on May 30, 2002 for a "Variable Repetition Rate Firing Scheme for Refractive Laser Systems," the full disclosure of which is incorporated herein by reference.

BACKGROUND OF THE INVENTION

The present invention is generally related to correcting optical errors of light refracted by eyes. In exemplary embodiments, the invention provides devices, systems, and methods for correction of optical errors of eyes which are particularly well-suited for the treatment of eyes during in situ keratomiliusis (LASIK), photorefractive keratectomy (PRK) and the like.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. The laser beam often comprises a pattern of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. The lasers of these laser systems typically deliver a series or pattern of laser beam pulses during a treatment.

It is generally desirable to complete a surgical procedure as quickly as possible. However, if the treatment occurs too quickly, the thermal effect on corneal tissue can become significant, potentially resulting in undesirable complications. For this reason, laser surgery systems generally employ fixed laser firing repetition rates which are sufficiently low for all intended operating modes. Unfortunately, this can result in extended treatment times which are uncomfortable for patients and time consuming for surgical staff. Also, it has been suggested that extended treatment times can vary tissue hydration that may change an amount of correction received by a patient.

In light of the above, it would be desirable to provide surgical ablation treatments having reduced treatment times while avoiding at least some of the limitations of known systems.

BRIEF SUMMARY OF THE INVENTION

The present invention provides systems and methods for applying pulsed energy to an eye. In an exemplary embodiment, a firing rate of the pulsed energy varies in correlation with a modeled or estimated thermal response of a tissue of the eye to the pulses of the laser beam during the treatment.

In one aspect, the invention provides a method for use in planning a corneal refractive procedure. The procedure comprises directing a pattern of ablative laser energy pulses toward a cornea. The method comprises determining a safe laser firing repetition rate based on a temperature change limit for the cornea and a relationship between a pulse characteristic and a rise in temperature of the cornea. The pulse characteristic varies according to the pattern.

In many embodiments, a plurality of differing pulse repetition rates are determined to define differing time delays between sequential pulses of the pattern. In some embodiments, the temperature change limit may comprise an acceptable safe change in temperature of corneal tissue between a first temperature of the tissue and a maximum desired temperature. The first temperature may comprise an initial equilibrium temperature of the cornea prior to the initiation of the procedure, or may reflect prior corneal heating or the like. When ambient temperature is used as the starting point, the first temperature will often be in a range from about 30–35° C., typically being about 33° C. This first temperature may be measured or may be an estimated temperature of corneal tissue. The maximum desired temperature will typically be selected so as to be less than a hyperthermia temperature of the corneal tissue, and will often be less than about 47° C., typically being less than about 44° C. This maximum desired temperature may be selected based at least in part on a period time for which the corneal tissue will be heated. The temperature change limit will often be less than about 12° C., ideally being 10 C. or less so as to maintain safety margins.

The relationship between the pulse characteristic and the rise in temperature will often comprise a correlation between temperature, repetition rate, and/or size of the laser beam spot incident on the cornea. The relationship may indicate a substantially linear change in the temperature for changes in the repetition rate for a given spot size. Similarly, when the pulse characteristic comprises the spot size of the laser beam, the relationship may indicate a decrease in spot size corresponds with an increase in allowable repetition rate within the limited allowable change in temperature.

In another aspect, the invention provides a system for use in planning a corneal refractive procedure. The procedure comprises directing a pattern of ablative laser energy pulses towards a cornea. The system comprises a module having at least one input for accepting the pattern. The pattern includes a pulse characteristic which varies within the pattern. The module defines a plurality of differing time delays between sequential pulses of the pattern based on a temperature limit of the cornea and a relationship between the pulse characteristic and a rise in temperature of the cornea.

In another aspect, the invention provides a method for planning a refractive procedure. The procedure comprises directing a pattern of ablative laser energy pulses towards a cornea of the eye. The system comprises inputting the pattern in a first order so as to define a first pattern. A second pattern is derived from the first pattern based on a corneal heating model by selectively determining a plurality of differing time delays between sequential pulses, and/or reordering the pulses of the first pattern. The second pattern is output to a laser system for ablating the cornea with the ablative laser energy according to the pattern.

The time delays will often be determined by identifying at least one initial safe laser firing repetition rate for the pulses. The initial time delays may be iteratively reduced, and the safety of the corneal thermal response may be verified with the reduced time delays. The initial repetition rate or rates will often be selected so as to result in a safe steady-state corneal tissue temperature if the associated pulses were repeated indefinitely.

Each pulse of the pattern may have an associated laser spot size, and the spot sizes of the pulses may vary according to the pattern. A series of initial thermally safe laser firing repetition rates may be identified in response to the spot sizes. The corneal thermal response of at least some of the pulses may be verified by integrating a plurality of prior pulses within a time window. The integrated prior pulses may have laser spots encompassing a first location. The first location may be a central pupil location, and the corneal thermal response of at least some of the pulses may also be verified at a plurality of outlying locations within a treatment region. The pulses within the time window may have different associated spot sizes, and the different spot sizes may have different associated allowable steady-state time delays. The thermal response of the cornea may be verified by combining the allowable time delays for the pulses of different spot sizes to a total time, and that total time may be compared to the time window. In some embodiments, when the pulses within the time window are scanned across the cornea, the first location may be outside of at least some of the laser spots of the scanned pulses. The thermal response can then be verified using an average pulse rate corresponding to the number of pulses having laser spots encompassing the first location during the time window.

Optionally, the pattern may comprise a series of laser spot locations across the cornea. The first pattern may be assigned a first order, and the deriving step may comprise reordering the pattern from the first order to a second order. The pattern of pulses in the second order may generate a lower estimated cornea temperature and/or a lower cornea treatment time than the pattern in the first order, even where the laser pulse locations, spot sizes, and numbers have not changed.

In another aspect, the invention provides a system for planning a laser refractive procedure. The procedure comprises directing a pattern of ablative laser energy pulses toward a cornea of the eye. The system comprises a memory for storing the pattern, and a corneal heating model. A module assigns a plurality of differing time delays between sequential pulses of the pattern based on the corneal heating model. An output communicates the time delays for ablation of the cornea.

In another aspect, the invention provides a system for planning a laser refractive procedure. The procedure comprising directing a pattern of ablative laser energy pulses toward a cornea of the eye. The system comprises a memory for storing the pattern in a first order so as to define a first pattern. A corneal heating model is coupled to the memory, and a module derives a second pattern from the first pattern by reordering the pulses of the first pattern based on the corneal heating model.

BRIEF DESCRIPTION OF THE DRAWINGS

FIGS. 11A–11C illustrate patterns of pulses stored in treatment tables, and how those patterns can be processed to decrease treatment times.

FIGS. 13A–13D graphically illustrate data used for determining the safe steady-state rates of FIG. 13.

FIGS. 14A–14D graphically illustrate the thermal response of corneal tissues to laser pulse patterns before and after processing the patterns with the method of FIG. 9A.

DETAILED DESCRIPTION OF THE INVENTION

The present invention is particularly useful for enhancing the safety and speed of laser eye surgical procedures, such as photorefractive keratectomy (PRK), phototherapeutic keratectomy (PTK), laser in situ keratomileusis (LASIK), and the like. While the system and methods of the present invention are described primarily in the context of a laser eye surgery system for treating a cornea of the eye, it should be understood the techniques of the present invention may be adapted for use in alternative eye treatment procedures and systems.

The techniques of the present invention can be readily adapted for use with existing laser systems. By providing a more rapid methodology for correcting optical errors of an eye, the present invention facilitates sculpting of the cornea so that treated eyes may regularly receive a desired optical correction having improved vision with minimal discomfort to a patient.

Figure 1:
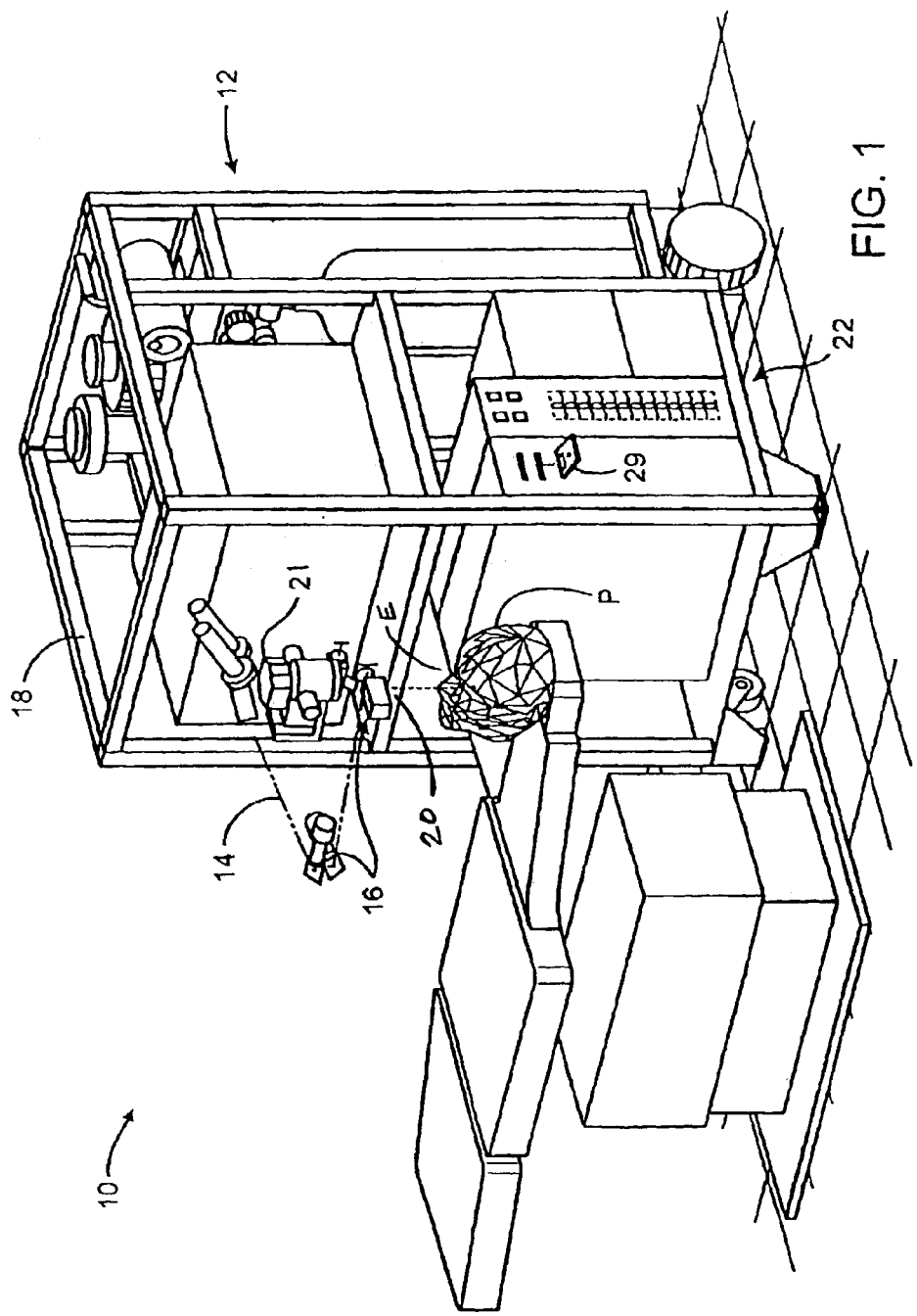
FIG. 1 is a perspective view of a laser ablation system for incorporating the invention.

Referring now to FIG. 1, a laser eye surgery system 10 incorporating the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. An input device 20 is used to align laser system 10 with patient P. A microscope 21 is mounted on the delivery optics support structure, the microscope often being used to image a cornea of eye E. In various embodiments, the laser eye surgery system 10 includes at least some portions of a STAR S3 ACTIVE TRAK™ EXCIMER LASER SYSTEM available from VISX, Incorporated of Santa Clara, Calif.

While the input device 20 is here schematically illustrated as a joystick, it should be understood that a variety of input mechanisms may be used. Suitable input mechanisms may include trackballs, touch screens, or a wide variety of alternative pointing devices. Still further alternative input mechanisms include keypads, data transmission mechanisms such as an Ethernet, intranet, internet, a modem, or the like.

Laser 12 generally comprises an excimer laser, ideally comprising an argon-fluorine laser producing pulses of laser light having a wavelength of approximately 193 nm. The pulse of laser light typically has a fixed pulse duration having a full width half maximum (FWHM) of about 15 nano seconds during a treatment. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193–215 nm) such as those disclosed in U.S. Pat. Nos. 5,144,630 and 5,742,626; Borsuztky et al., "Tunable UV Radiation at Short Wavelengths (188–240 nm) Generated by Sum Frequency Mixing in Lithium Borate", Appl. Phys. 61:529–532 (1995), and the like. The laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to the eye E of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible media 29 in the form of a treatment table, and the treatment table may be adjusted according to feedback input into processor 22 from an automated image analysis system (manually input into the processor by a system operator) in response to feedback data provided from an ablation monitoring system feedback system. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Ser. No. 09/274,999 filed Mar. 22, 1999, the full disclosure of which is incorporated herein by reference. Still further alternatives are possible, including scanning of the laser beam over a surface of the eye and controlling the number of pulses and/or dwell time at each location; using masks in the optical path of laser beam 14 which ablate to vary the profile of the beam incident on the cornea; hybrid profile-scanning systems in which a variable size beam (typically controlled by a variable width slit and/or variable diameter iris diaphragm) is scanned across the cornea; or the like. Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference.

Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal topography map, a measurement of refraction of the eye, and/or an ablation table. Optionally, the portion of processor 22 on which some of all of the methods described below are executed may be integrated into a diagnostic system such as a Wavescan™ wavefront system for determining an ablation shape, and may interface with a separate processor of the laser system. A variety of alternative distributed processing arrangements are possible, as are a number of data transfer modalities.

Figure 1A:
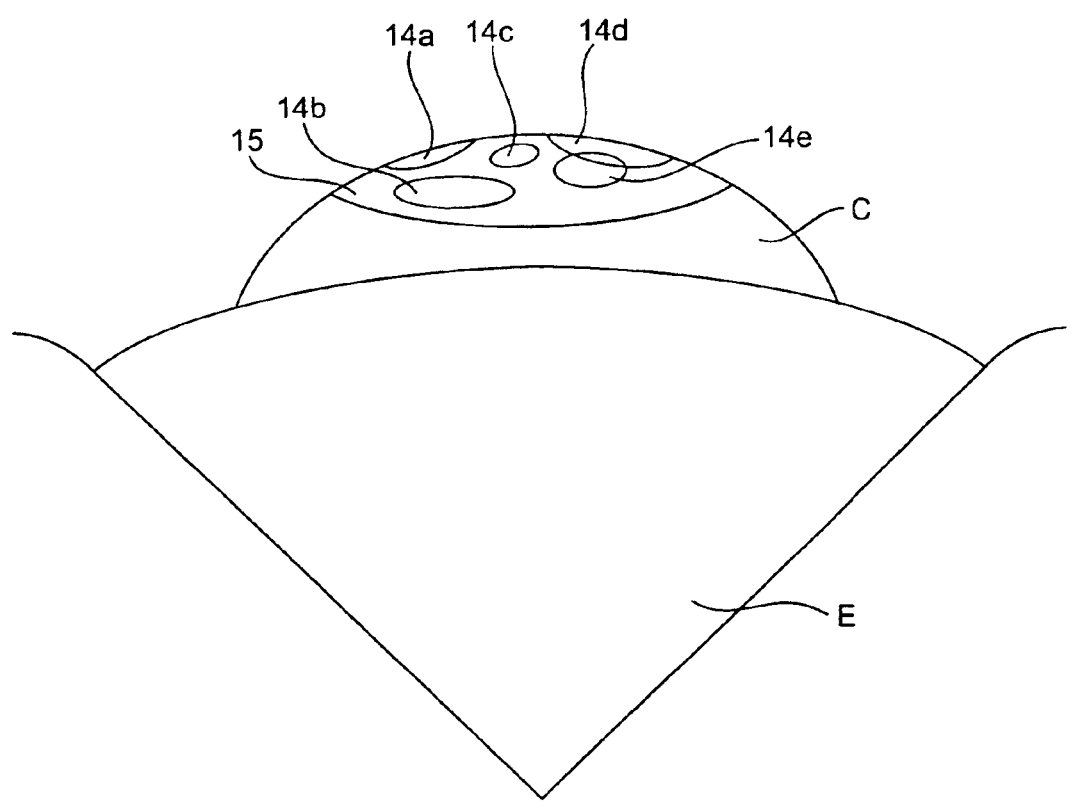
FIG. 1A illustrates an ablation of an eye using a series of scanning laser beam pulses of varying diameter applied over a treatment area of a cornea of an eye.

An ablation of an eye using a series or pattern of pulses 14a–14e of a scanning laser beam is schematically illustrated in FIG. 1A. The series of pulses are applied over a treatment area or region 15 of a cornea C of an eye E. As illustrated in FIG. 1A pulses 14e and 14d generate laser spots which overlap. A dimension across pulse 14c is smaller than a dimension across pulse 14b. The pattern of pulses 14a to 14e are sequentially applied to eye E, with the pattern defining the locations and size of the laser spots incident on the cornea.

Figure 2:
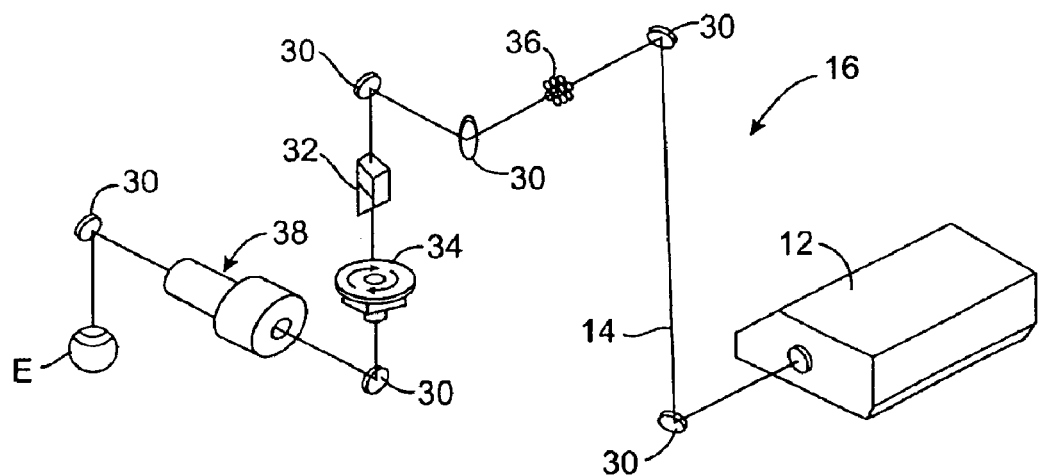
FIGS. 2 and 3 schematically illustrate a laser beam delivery system for selectively directing a laser beam onto the corneal tissue.
Figure 3:
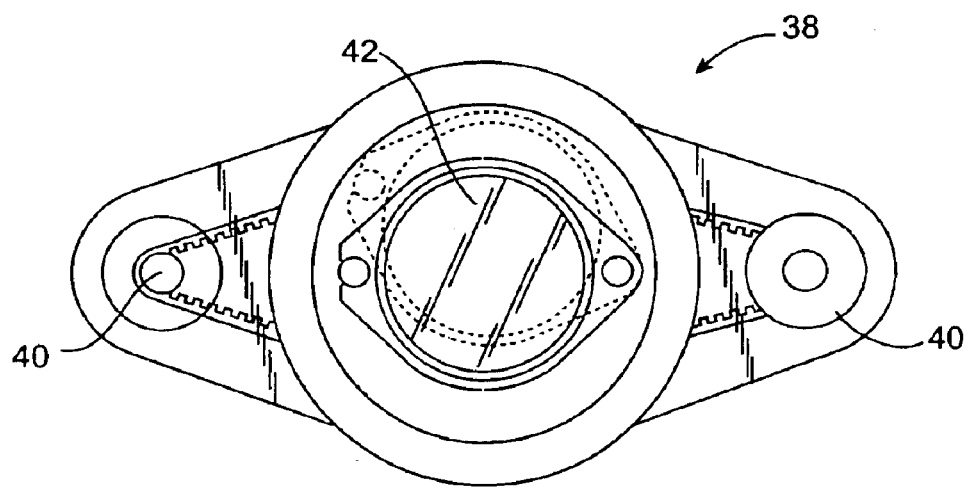

Referring now to FIG. 2, laser beam delivery system 16 for directing laser beam 14 at eye E will often include a number of mirrors 30, as well as one or more temporal integrators 32 which may even (or otherwise tailor) the energy distribution across the laser beam. Laser 12 will often comprise an excimer laser as described above. A variable aperture 34 changes a diameter and/or slot width to profile laser beam 14. A prism 36 separates laser beam 14 into a plurality of beamlets, which may partially overlap on eye E to smooth edges of the ablation or "crater" from each pulse of the laser beam. Referring now to FIGS. 2 and 3, an offset module 38 includes motors 40 which vary an angular offset of an offset lens 42, and which also change the radial orientation of the offset. Hence, offset module 38 can selectively direct laser beam 14 at a desired lateral region of the cornea. A structure and method for using a related laser beam delivery system and offset module are more fully described in U.S. Pat. No. 6,488,676, the full disclosure of which is incorporated herein by reference.

Figure 4:
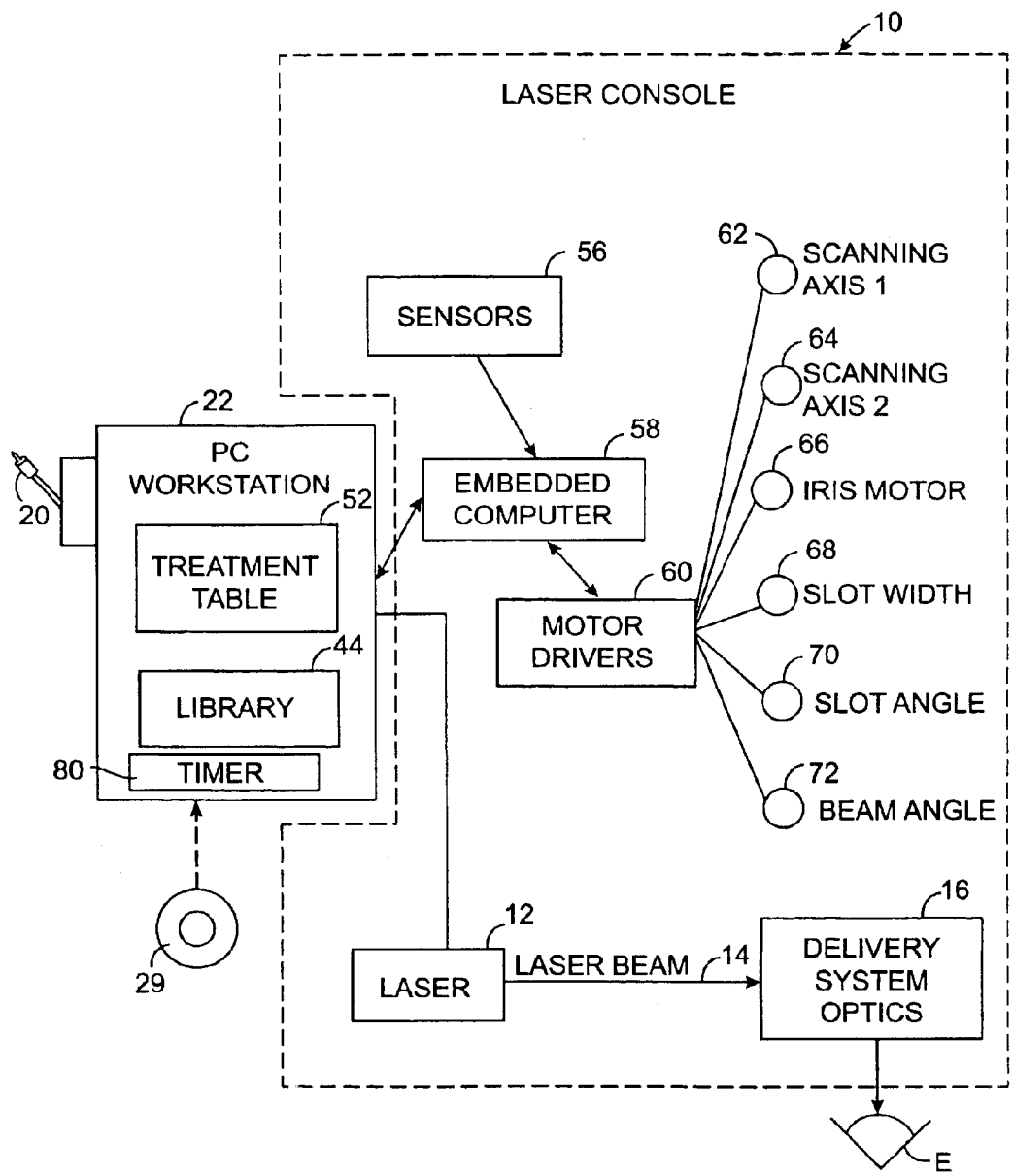
FIG. 4 is a function block diagram illustrating a control architecture of an ablation system as in FIG. 1.

Referring now to FIG. 4, a control system of a laser system 10 includes a processor 22 which enables precise control of laser system 10 to sculpt a surface shape specified in a laser treatment table 52. Processor 22, which generally comprises a PC workstation, makes use of a computer program stored on a tangible media 29 to generate treatment table 52. Processor 22 includes a library 44 of treatments as described in U.S. Pat. No. 6,245,059, the full disclosure of which is incorporated herein by reference. An embedded computer 58 within laser system 10 is in electronic communication with the PC workstation. Alternatively, a PC workstation may be embedded in the laser system and include an embedded processor card in communication with the PC workstation for directing the ophthalmic surgery.

Embedded computer 58 is in electronic communication with a plurality of sensors 56 and a plurality of motor drivers 60. The motor drivers 60 are coupled to the embedded computer 58 to vary the position and configuration of many of the optical components of the delivery optics 16 according to treatment table 52. For example, first and second scanning axis 62, 64 control the position of the offset lens to move the beamlets over the surface of the cornea. Iris motor 66 controls the diameter of the overall beam, and in some cases, the length of light transmitted through a variable width slot.

Optionally, the laser system may rely on an iris to change the laser spot size, without use of a variable slot for some or all treatments. When a slot is used, similarly slot width driver 68 controls the width of the variable slot. Slot angle driver 70 controls rotation of the slot about its axis. Beam angle driver 72 controls rotation of the beam as effected by a temporal integrator as described above. Processor 22 issues a command for laser 12 to generate a pulse of the laser beam 14 after the various optical elements have been positioned to create a desired crater on eye E. Treatment table 52 comprises a listing of all of the desired craters to be combined so as to effect a treatment therapy.

A timer 80 is located on an add on card of processor 22 and may optionally comprise a Lab-PC-1200 model card having timers 8253/8254. The Lab-PC-1200 model card is available from NATIONAL INSTRUMENTS of Austin, Tex. In alternate embodiments, timer 50 is located externally to processor 22. The timer 80 is controlled by a computer program of processor 22 and is adapted to measure time intervals. The laser 12 is electronically coupled to processor 22. Laser 12 fires upon a command issued from processor 22 in response to a time interval measured by timer 80. Processor 22 varies the rate at which laser 62 fires during at least a portion of a treatment of an eye E.

Figure 5:
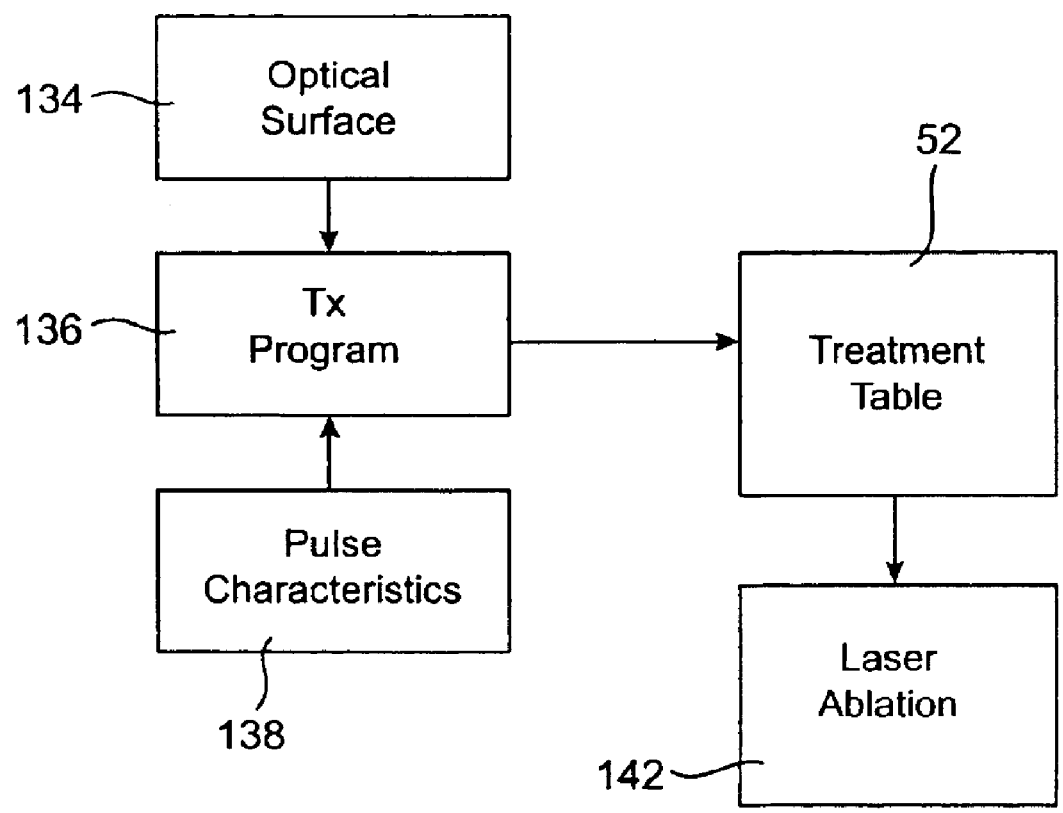
FIG. 5 is a flow chart schematically illustrating a method for determining a corneal ablation treatment program.

A flow chart schematically illustrating one method for determining a corneal ablation treatment program is illustrated in FIG. 5. A treatment program 136 may be calculated from an optical surface 134 so as to remove the regular (spherical and/or cylindrical) and irregular errors of the optical tissues. Methods and systems for determining optical surface 134 are described in U.S. Pat. Nos. 5,163,934 and 6,271,914, the full disclosures of which are herein incorporated by reference. By combining the treatment program 136 with laser ablation pulse characteristics 138 of a particular laser system, a treatment table 52 of ablation pulse locations, sizes, shapes, and/or numbers can be developed. An exemplary method and system for preparing such an ablation table is described in co-pending U.S. patent application No. 60/189,633, filed on Mar. 14, 2000, and entitled "*Generating Scanning Spot Locations for Laser Eye Surgery,*" the full disclosure of which is incorporated herein by reference.

The individual pulses of treatment table 52 may optionally be sorted so as to avoid localized heating, minimize irregular ablations if the treatment program is interrupted, and the like, as described below. Preferably, the treatment table is sorted to apply small diameter pulses to an eye initially followed by large diameter pulses. Alternatively, a treatment table may be sorted to apply large diameter pulses to an eye initially followed by smaller diameter pulses, and an order of pulses may even have a random size distribution. As also described below, the treatment table may be sorted or otherwise processed using a thermal model of corneal tissue. The eye can then be ablated according to the processed treatment table 52 by laser ablation 142.

Figure 6:
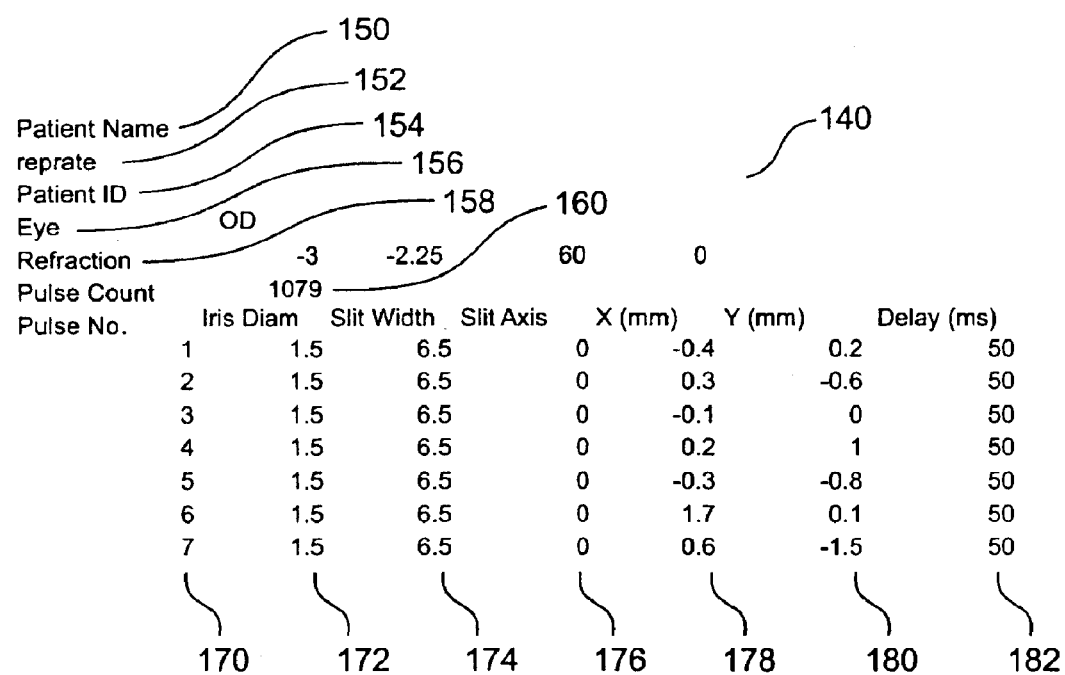
FIG. 6 illustrates a laser treatment table in accord with an embodiment the invention.

Referring now to FIG. 6, several listings from an exemplary laser treatment table 140 are illustrated. A Patient Name 150, patient identification number (Patient ID) 154, and treated Eye 156 are listed in table 140. A repetition rate (rep rate) 152 is also listed. As shown in FIG. 2B repetition rate 152 is selected to be variable. A refraction 158 having a sphere of −3 D, a cylinder of −2.25D, an axis of 60 degrees and a vertex distance of 0 mm is listed in FIG. 6. A pulse count 160 as listed in FIG. 6 illustrates a total number of 1079 pulses applied during a treatment. Additional fields of treatment table 140 are pulse number 170, iris diameter 172, slit width 174, slit axis 176, X coordinate 178, Y coordinate 180 and delay 182.

For each pulse of treatment table 140, the pulse number 170, iris diameter 172, slit width 174, slit axis 176, X coordinate 178, Y coordinate 180 and delay 182 are listed. The X coordinate 178 and Y coordinate 180 list the X and Y coordinates of the center of each pulse on the cornea relative to a treatment center during a treatment as described above. The iris diameter field 172 lists the dimension across a circular diaphragm opening as projected onto the eye in mm for each pulse during treatment as described above. The slit width 174 and slit axis fields 176 list the dimension across a variable width slot opening as projected onto the eye in mm, and the angle of the slot opening with respect to the eye in degrees as described above. The delay 182 lists the delay in ms to the next pulse of the treatment. The firing rate 208 of the laser is the inverse of the delay 206. As shown in FIG. 6, the delay is 50 ms for each pulse, which produces a 20 Hz firing rate of laser system 10. For a complete treatment, the delay varies from 125 to 50 ms, and the cross sectional dimension of the beam varies from 1.5 mm to 6.5 mm.

Figure 7:
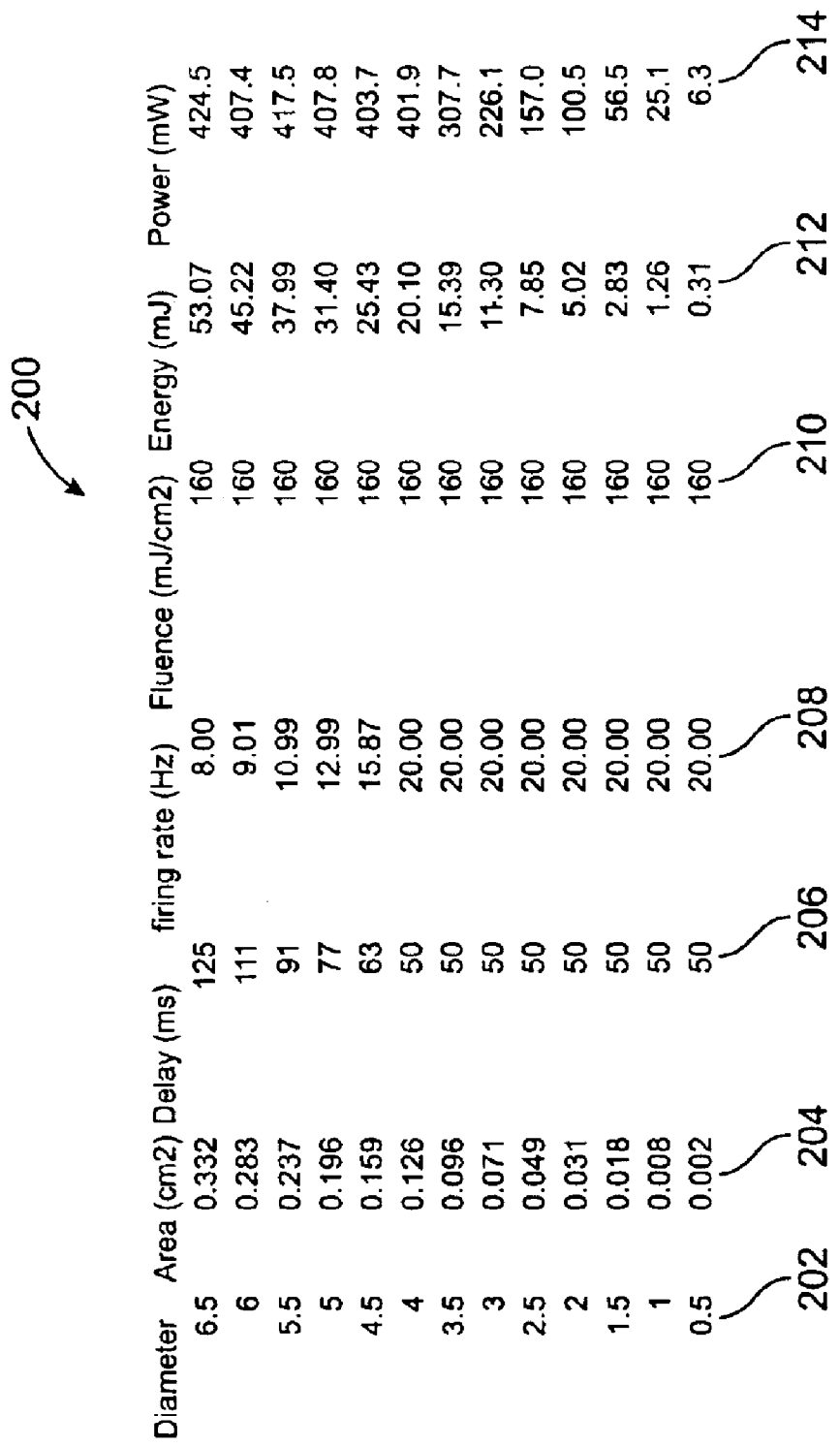
FIG. 7 illustrates treatment diameters and laser firing rates in accord with an embodiment of the invention using a variable laser firing rate for a first portion of a treatment and a fixed firing rate for a second portion of a treatment.

For each pulse diameter and pulse energy applied to the eye, a delay until the next pulse is illustratively summarized in FIG. 7. Delay 206 is listed for each beam diameter 202. A diameter of an iris in mm 202 provides a beam at the surface of the eye having a cross sectional area 204. For an average fluence 210 for each pulse of 160 mJ/cm2, an energy 212 applied to the eye with a pulse of the laser beam is equal to the product of the area 204 and fluence 210. For each diameter 202 listed, the power 214 applied to the eye is the product of the energy applied to the eye with each pulse 212 and the firing rate 208 in Hertz of the laser. For example, for a 5 mm beam diameter the cross sectional area the beam is 0.196 cm$^2$ and the energy applied to the eye is 31.4 mJ with each pulse. The firing rate 208 of the laser 12 is 12.99 Hz and the power 214 applied to the eye is 407.8 mW.

As shown in FIG. 7, the firing rate of the laser is constant for a first portion of a treatment having pulses from 0.5 to 4 mm, and variable for a second portion of the treatment having pulses from 4 mm to 6.5 mm. The laser firing rate may be limited to improve system reliability and prevent system heating. For example, as shown in FIG. 3A, the laser firing rate is limited to no more than 20 Hz.

A laser firing rate of laser system 10 may vary from the values listed in a treatment table. For example, a closed loop system measures a position of several moving elements as described above, and may delay firing of the laser system until each of the several moving elements are positioned. Should positioning of at least one moving element take longer than the firing and delay, the laser pulse is delayed until the element is correctly positioned. Also, an eye tracking system may delay a pulse of a treatment in response to a rapidly moving eye or an eye that has temporarily moved beyond a limit, for example an eye with a nystagmus.

Figure 8:
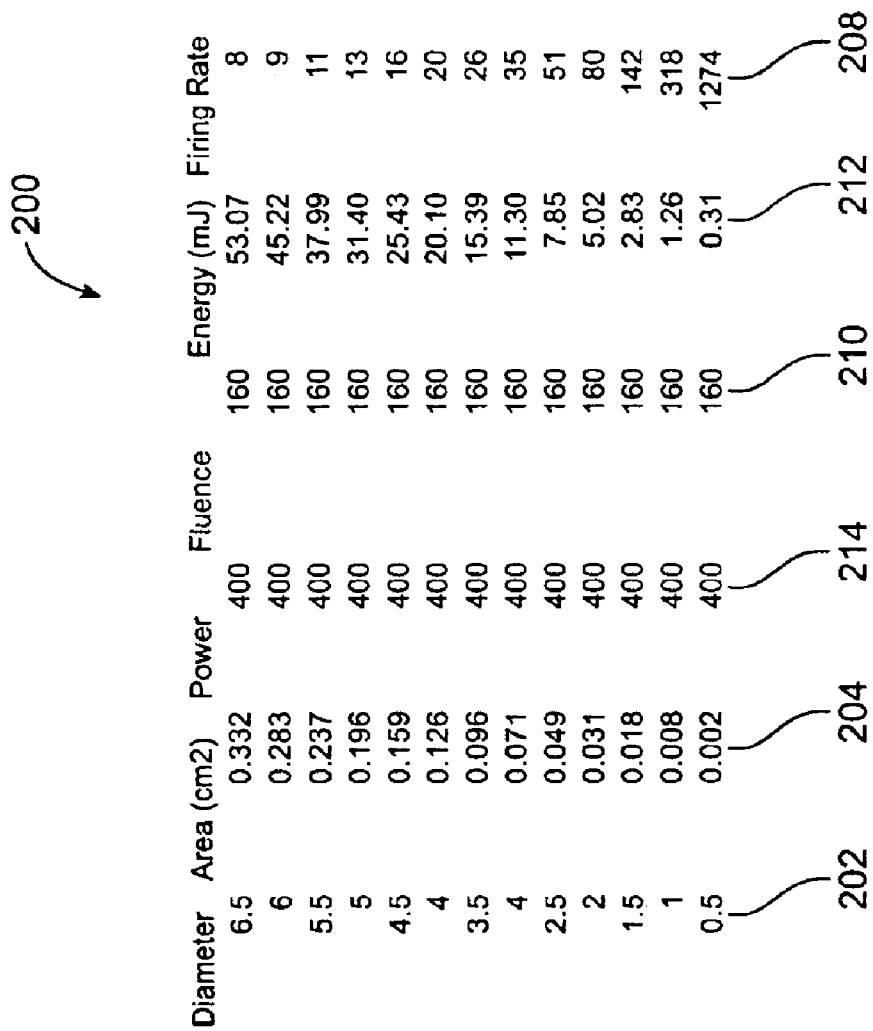
FIG. 8 illustrates variable treatment diameters and laser firing rates arranged so as to maintain a power of the beam applied to the eye at a substantially constant level in accord with an embodiment of the invention.

Firing rates for a laser having a nearly constant power of 400 mW applied to an eye are illustrated in FIG. 8 for a treatment using different amounts of energy with several pulses of a laser beam. Any power level, range of beam diameters and range of firing rates can be selected to deliver a desired amount of optical power to eye E of patient P. As illustrated in FIG. 8 a beam diameter 202 of 3 mm at the eye provides a per pulse energy 212 of 11.3 mJ for an average fluence 210 of 160 mJ/cm$^2$. To provide a power 214 of 400 mW to the eye, a firing rate of 35 Hz is used during treatment. For a beam diameter 202 of 1 mm having a per pulse energy 212 of 1.26 mJ, a firing rate of 318 Hz is used. A range of beam diameters is from about 1 to 3 mm and a firing rate of the laser is from about 35 Hz to 318 Hz.

Figure 9A:
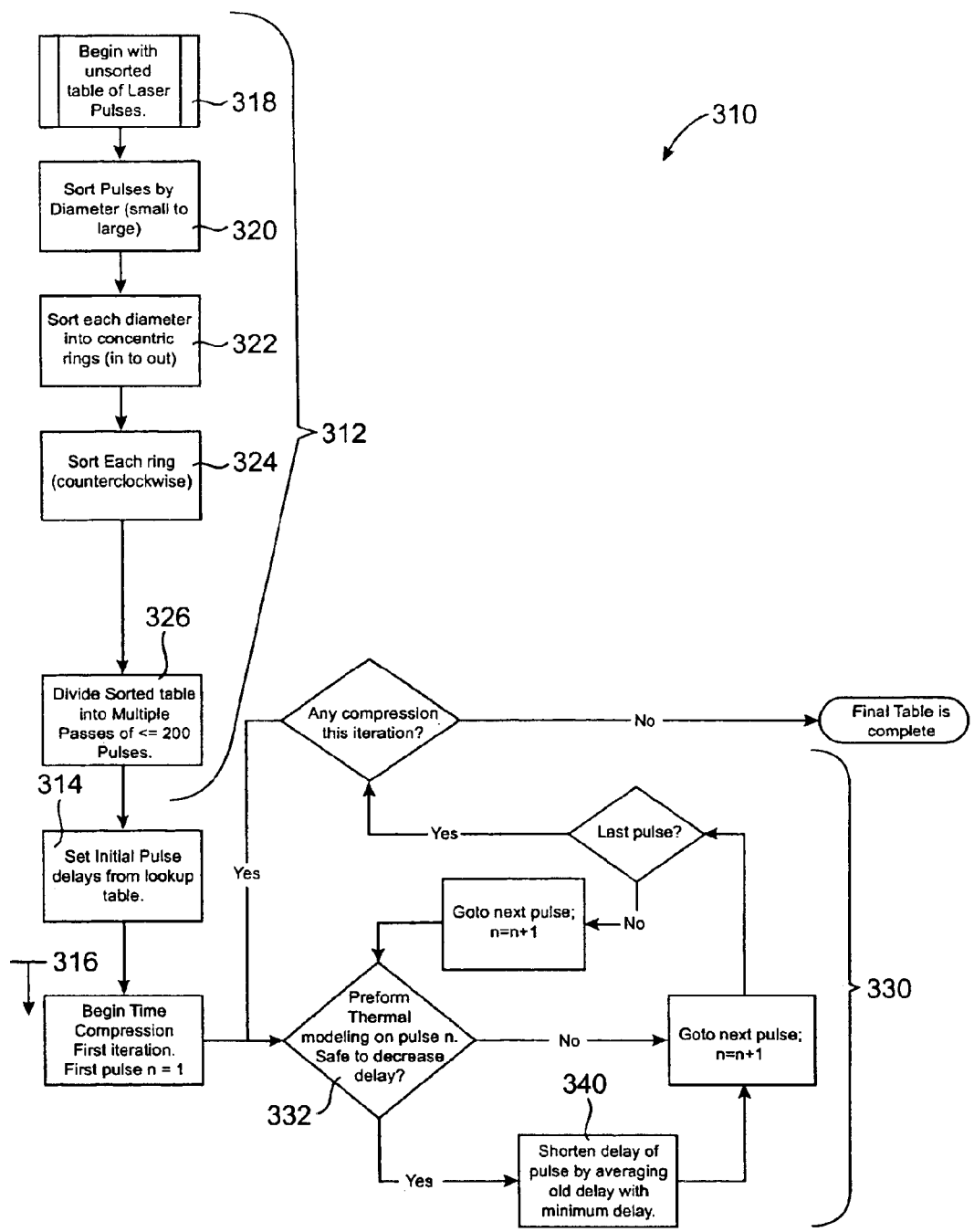
FIG. 9A is a flow-chart illustrating method steps for deriving a treatment table based on a thermal model of corneal tissues.
Figure 9B:
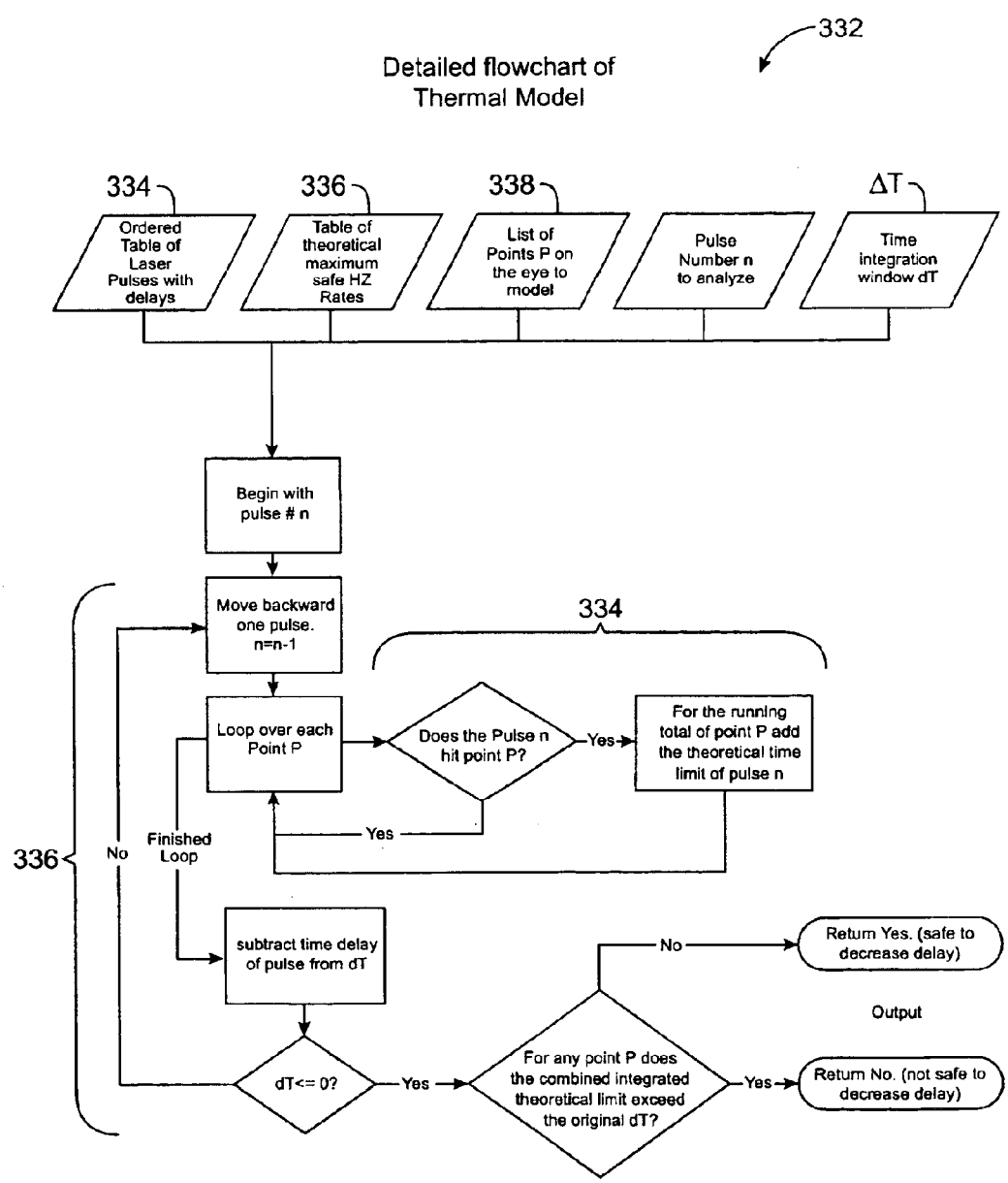
FIG. 9B is a flow-chart illustrating method steps for modeling the thermal response of corneal tissue to laser refractive surgery pulse patterns.

Referring now to FIGS. 9A and 9B, the present invention also provides systems and methods for planning a corneal refractive procedure by making use of thermal modeling of the corneal tissues so as to safely decrease overall procedure times. The method steps illustrated in FIGS. 9A and 9B will often be embodied in a tangible media as machine readable code. The machine-readable code may comprise program steps, and may be embodied in a volatile or long-term memory, a magnetic or optical recording media, hardware, software, firmware, or the like. The program steps may be executed by a processor of the laser system, a stand alone processor, or a processor of an associated diagnostic device such as the processor of a Wavescan™ wavefront system, as noted above. In many embodiments, an initial pattern of laser pulses will be determined by a separate processor or separate software module before initiation of the methods of FIGS. 9A and 9B. The pattern of laser pulses will typically be input and/or stored in the form of a table, with the table often having an initial order (along with pulse locations, laser spot size, and the like) as described above. The methods of FIGS. 9A and 9B may be performed by a variety of different processing modules which may comprise software, hardware, and/or a mix of software and hardware, with the input and output optionally being effected by transmission of data along a signal conduit, identification of a memory location, recording on a tangible media or the like.

Preferably, these methods will be performed using a processor having at least the capability of a PENTIUM™ processor or more, such as a PENTIUM II™ processor or a PENTIUM III™ processor.

A thermal model-based treatment time compression method 310 illustrated in FIG. 9A generally comprises three major portions: in a first portion 312 in which a pattern of laser pulses is input and sorted; a second portion 314 which establishes initial time delays between sequential pulses of the sorted pattern; and a third portion 316 in which the duration of the treatment is systematically shortened in an iterative process.

Sorting portion 312 generally begins with a complete table defining the pattern of laser pulses capable of achieving the desired change in refractive properties of the eye at start 318. As noted above, the pulses may be sorted by ordering the pulses based on the spot size 320. Pulses having common spot sizes may then be sorted or grouped together so as to define concentric rings or bands, spiral arms curving radially outwardly and circumferentially from a treatment center, or the like in a second sorting step 322. These individual groups may then be sorted in a third sorting step 324, for example, so as to order the pulses within the group to direct laser spots in a sequentially counter-clockwise progression. These initially sorting steps decrease mechanical motion time by avoiding large unnecessary changes in the iris diaphragm or other aperture. Similarly, motion of the scanning mechanism between sequential pulses can be limited.

The final sorting step 326 involves separating of the table into multiple passes, with the total number of pulses in each pass optionally being maintained below some target number (such as 200 pulses, typically being between 50 and 500 pulses). The number of passes may be identified by dividing the total number of pulses by the greatest number of pulses allowed in a pass. The table may then be separated into the identified number of separate passes or sub-treatments by assigning the first pulse of the treatment to the first pass, the second pulse of the treatment table to the second pass, and so on until each of the passes has a first pulse assigned thereto. Thereafter, the next pulse of the treatment table is assigned to the first pass, the following pulse to the second pass, and so on. This results in a reordered treatment table which has a larger amount of actuator movement between sequential pulses than the table resulting from treatment steps 318 through 324. However, the total actuator movement between pulses remains relatively limited (for example, in a 4-pass treatment table the actuator motion may be four times greater than that of the treatment table resulting from step 324, but typically will not require scanning of the pulse locations back and forth across the cornea, or repeated major closing and opening of the aperture, within a few sequential pulses of each pass). This sorting or separation of the treatment into passes has the benefit of spreading the thermal energy delivered to a particular location on the cornea out over time.

The setting of an initial pulse delay 314 will establish a time delay or firing rate of the laser between sequential pulses, as generally described above. The initial pulse delays (the pulse period or time between firing of two sequential pulses) may be established based on characteristics of the individual pulses, so that the initial delays vary throughout the treatment table. The initial pulse delays will often depend on the size of the associated laser spot. In some embodiments, the initial pulse delay may be uniform throughout the treatment table, or may vary in response to a location of the laser spot, for example, relative to other prior laser spots, their overlap with the subject laser spot, and the like.

The exemplary initial pulse delays will comprise safe steady-state laser firing delays. The underlying corneal tissue may undergo a temperature rise when subjected to repeated pulses, with the quantity of temperature rise varying according to the characteristics of the laser pulse. The temperature rise may increase with an increasing firing rate (or a decreasing delay between pulses), and will eventually reach a steady-state temperature. Hence, for a given allowable maximum corneal tissue temperature and a given laser pulse size, energy, and location, a maximum steady-state pulse repetition rate may be defined.

By setting the initial pulse rate of the table at the maximum safe steady-state pulse rate, the corneal tissue temperature can generally not be driven beyond a maximum safe tissue temperature, even if the pulse is repeated indefinitely. However, this fails to take advantage of the scanning of the laser spots across the cornea so as to distribute any heating, and also neglects the changes in pulse characteristics the treatment table may impose at a particular location. The result of these factors may be that heating of the corneal tissue remains well below a safe maximum and/or that the treatment time is longer than it need be when the steady-state pulse rates are applied. For this reason, method 310 includes an iterative loop 330 to systematically shorten the individual pulse delays, and to verify that the thermal response of the corneal tissue remains acceptable using a thermal model 332.

Figure 13:
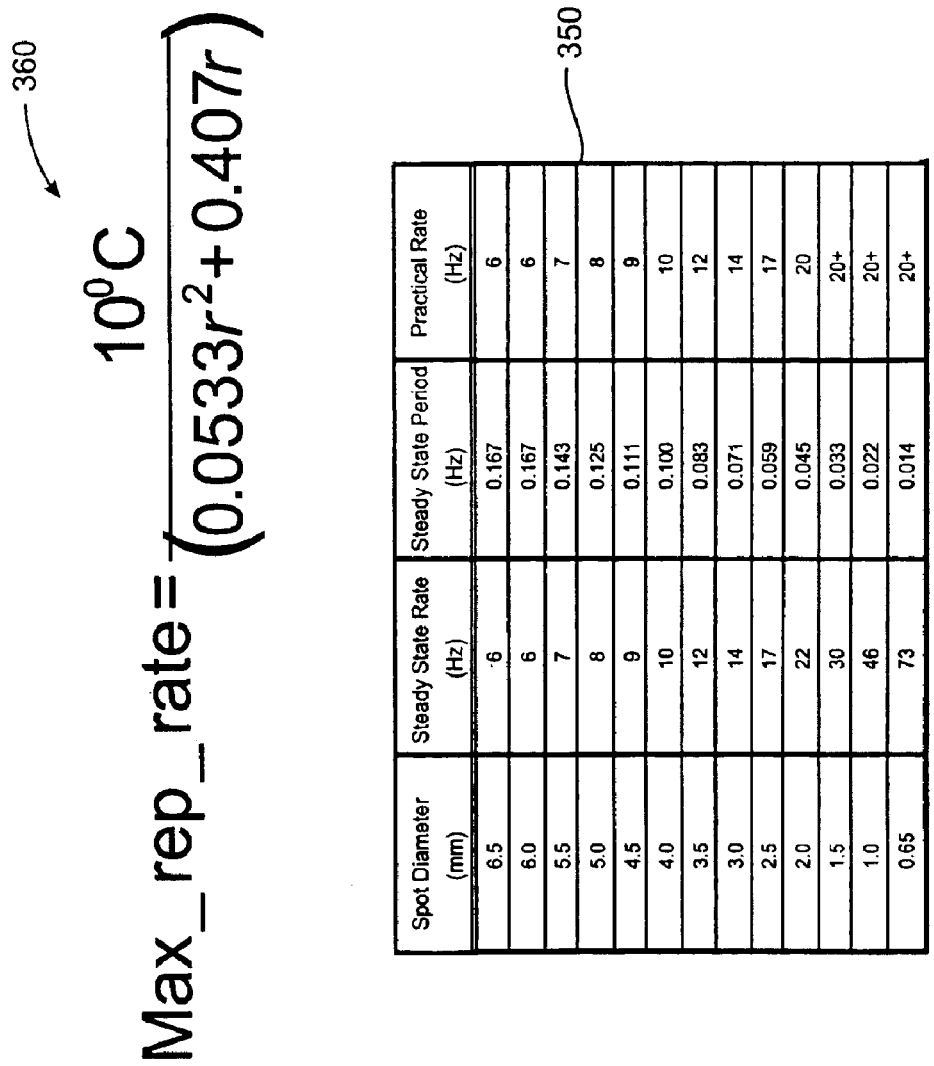
FIG. 13 is a table of safe steady-state laser firing rates for different laser spot diameters, along with a formula for calculating these steady-state rates.

Thermal model 332 is illustrated in more detail in FIG. 9B. The thermal model generally takes as input the sorted table of pulses with their associated delays 334, along with the maximum steady-state laser firing rates or delays times for different pulse characteristics 336. These safe steady-state firing rates may be in the form of a lookup table or equation as seen in FIG. 13. Additional input to the thermal model include points P1, P2, . . . on the eye at which the thermal response of the corneal tissue will be modeled, as designated by input 338. Thermal model inputs also include the specific pulse number to be analyzed, along with a time period or window $\Delta T$ during which pulses will be integrated.

Figure 10:
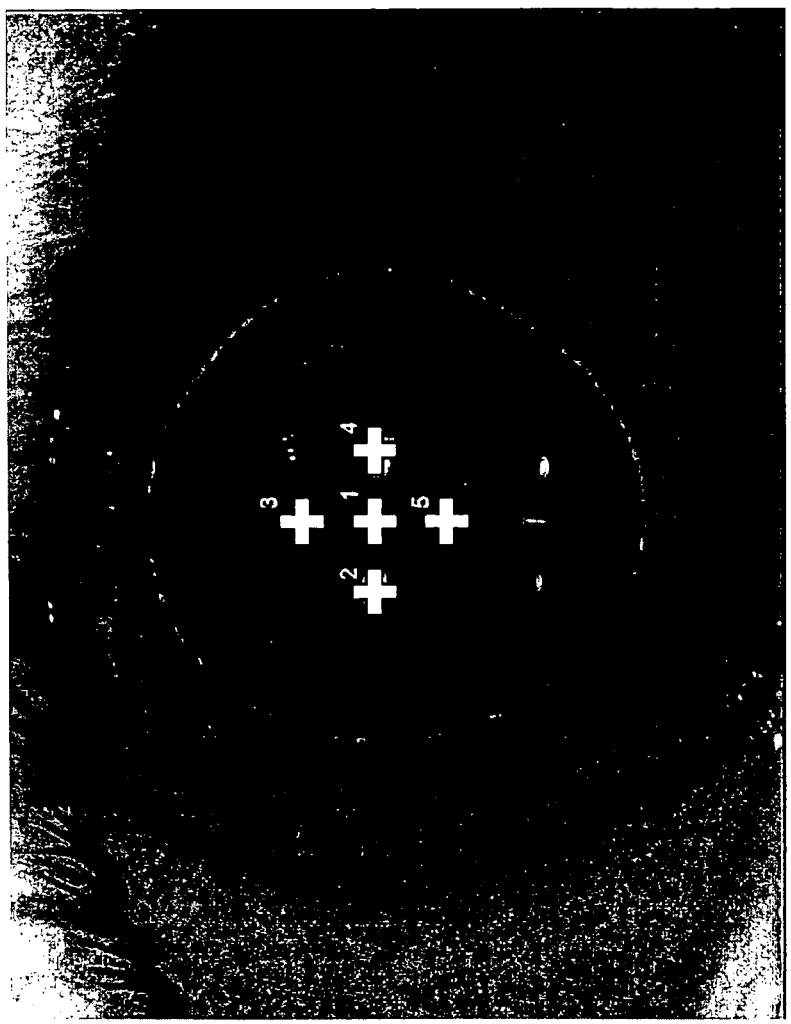
FIG. 10 illustrates central and outlying thermal modeling locations within a treatment region of a cornea.

As can be understood with reference to FIGS. 9B, 10, and 11B, along with FIG. 1A, for any given point P on the cornea, a particular laser pulse may or may not generate a laser spot encompassing that point. As the corneal thermal response from the laser spots will be localized across the cornea, a central location P1 and a series of outlying locations P2 through P5 within the treatment region are separately modeled to verify that localized thermal response of the corneal tissue does not exceed safe limits. To take advantage of the distributed thermal effects of scanning of the laser spots, only points actually encompassed by a laser spot of a particular pulse will be considered to have a thermal effect at that point. The location of the points P1, P2, . . . may reflect a general tendency of the thermal effects to be greatest near a center of the treatment region, and the spacing between pulses may be such as to avoid laser spots falling between the discrete thermal modeling locations. In any event, the thermal model will generally loop through each point P1, P2, . . . , and will consider only those pulses having laser spots encompassing the point in a discrete point loop 334 (as marked by an "X" in FIG. 11B).

Thermal model 332 generally decreases the overall time for a photorefractive procedure by determining whether or not if is it safe to decrease the delay (or increase the firing rate) for a specific pulse #n using a loop 336 which integrates backward in time by $\Delta T$ seconds. This backward integration follows three mathematical rules. First, the thermal response at a particular location on the eye will result in a temperature rise less than the maximum safe temperature limit if that location is subjected to pulses at or below the safe steady-state firing rate. Second, laser pulses having differing pulse characteristics can be combined within a given time window $\Delta T$ if the steady-state time delays for the individual pulses remain less than the total time window $\Delta T$. For example, pulses having different diameters have different steady-state firing rates. Nonetheless, these different pulse diameters can be combined within a time window if the time delays associated with those pulses are less than the total time. Specifically applying the steady-state time delays or periods from FIG. 13, in a given second you can safely ablate a particular location on a cornea with four pulses of 5 mm, three pulses of 3.5 mm, and seven pulses of 1.5 mm, because $(4 \cdot 0.125)+(3 \cdot 0.083)+(7 \cdot 0.033)=0.98$, which is less than one second.

The third thermal modeling rule is that the safe steady-state rate may be an average rate of pulses over time window $\Delta T$. For example, again referring to the table of FIG. 13, if $\Delta T$ is equal to 4 seconds, we can subject a particular location of the cornea to 2 full seconds of 4 mm pulses at 20 Hz, followed by 2 seconds of no pulses, even though the steady-state rate for a 4 mm pulse is 10 Hz (delay times 0.1 second). This is because $2 \cdot 20$ Hz=40 pulses, and $40 \cdot 0.1=4$. which is less than or equal to $\Delta T$ These three rules generally hold true as long as $\Delta T$ is significantly less than the time it takes for the cornea to reach steady-state temperature.

Referring again to loop 336 of FIG. 9B, the thermal model focuses on one pulse at a time. For each point P hit by that laser pulse, the loop integrates backward in time by $\Delta T$ seconds. If none of the points have a summed theoretically time limit greater than or equal to $\Delta T$ then the time of pulse P will be reduced.

Figure 12:
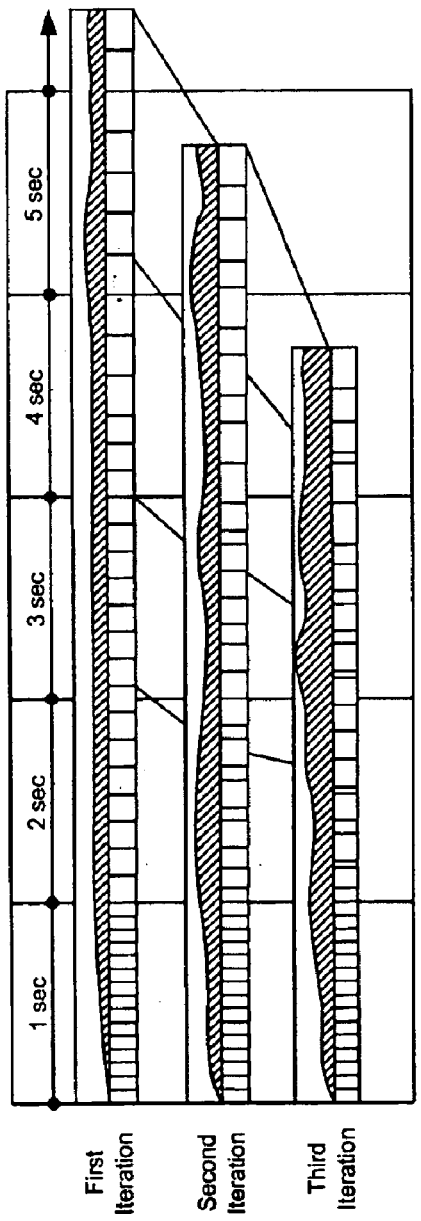
FIG. 12 graphically illustrates iterative processing of treatment patterns so as to decrease selected time delays between sequential laser pulses and reduce overall treatment time.

The pulse time is reduced in step 340 seen in FIG. 9A. The amount of reduction will be a fraction of the maximum allowed, which may be based on the greatest allowed firing rate of the laser. This technique can be generally referred to as successive over relaxation (SOR). Referring to a first table 342, illustrated in FIG. 11A, the setting of the pulse delays makes use of steady-state periods 346 such as those shown in FIG. 13. These initial time periods may reflect laser limitations (for example, if a laser is incapable of firing at a rate greater than 20 Hz, that may set the minimum time delay between sequential pulses). The initial times may also reflect required actuator movement time. These and other factors may also limit the final time delays of a time reduced or second treatment table 344 as shown in FIG. 11C. Once the treatment table has been sorted and assigned initial pulse delays, the program can analyze the table at each of the reference points and determine which points are hit by the laser spots of each pulse 348, as illustrated in FIG. 11B. The pulse packing loop 330 of method 310 may then iterate through the table to bring it toward the minimum time. Iterative successive over-relaxation technique is beneficial, because each change in a pulse duration effects all subsequent pulses. Processing the table iteratively allows the optimization to spread until no additional improvement in treatment time is provided. This "pulse packing" is schematically illustrated in FIG. 12.

Referring now to FIG. 13, table 350 sets forth steady-state laser firing rates for laser pulses having differing spot diameters along with associated steady-state periods. A practical rate is also given which is a modified form of the steady-state rate in which the laser structure capabilities are taken into account. A maximum allowable steady-state rate equation 360 is also shown in FIG. 13, in which the steady-state rate Max_rep_rate for an exemplary laser system may be calculated from a radius r of the laser spot. Such a steady-state rate table or equation may be determined empirically and/or derived through thermodynamic analysis of the corneal tissue response. This equation reflects an allowable change in temperature of the corneal tissue from an initial equilibrium temperature to a maximum safe temperature of about 10° C. Corneal surface temperatures of patients may be measured using a variety of thermal measurement techniques, such as FLIR thermal cameras or the like. A maximum safe tissue temperature may be derived from corneal tissue hyperthermia studies, which indicate that the survival fraction decreases dramatically when tissue is maintained at temperatures at or above about 46° C. As laser refractive procedures tend to be of limited duration (often being less than 10 minutes, typically being less than 5 minutes, and in many cases being less than a minute and a half) maintaining the corneal tissues below about 43° C. should provide a reasonable margin of safety. This results in an allowable temperature rise of less than about 12° C., ideally being 10° C.

The corneal temperature for a normal eye prior to treatment is fairly constant, with the eye showing little change in temperature even after being kept open for 2 minutes. A light air flow across the eye may cool the cornea a few degrees, with cooling from evaporation of the tear layer being a relatively small factor as compared to eye drops, air flow, and the like.

Referring now to FIGS. 13A through 13D, temperature studies made using a FLIR prism DS thermal camera show (in FIG. 13A) a horizontal cross section of the temperature across a porcine eye at thermal equilibrium in a bath of water at 37° C. FIG. 13B illustrates the corneal temperature rise in a central portion of a stationary 2 mm spot ablating an enucleated porcine eye at differing repetition rates. This data indicates the following equation may be used to determine the temperature rise at differing repetition rates rep_rate:

$$\Delta T' = 0.4638(rep\_rate)$$

Hence, to stay under a 10° C. temperature rise, the maximum steady-state repetition rate would be 10÷0.4638 is equal to about 21 Hz. Additional measurements of temperatures during scanning laser ablation procedures at differing spot diameters are illustrated in FIGS. 13C and 13D.

Using the above equation for steady-state temperature rise of a 2 mm spot size, and assuming the rate of temperature change is proportional to the incident power, for a 6 mm spot we can determine that:

$$C = \frac{\Delta T'}{rep\_rate} = \frac{17°\, C.}{10\, Hz} = 1.7 \left[\frac{°\, C.}{Hz}\right]$$

From similar computations and measurements, it can be shown that for a typical laser treatment, the relationship between spot diameters and corneal thermal response at 10 and 20 Hz repetition rates is given by Table 1:

TABLE 1

| | PTK TEMPERATURE | |
|---|---|---|
| Spot Diameter | 10 Hz [° C.] | 20 Hz [° C.] |
| 6 | 17 | 34 |
| 5 | 13.5 | 27 |
| 4 | 10.3 | 20.6 |
| 3 | 7.3 | 14.3 |

TABLE 1-continued

| | PTK TEMPERATURE | |
|---|---|---|
| Spot Diameter | 10 Hz [° C.] | 20 Hz [° C.] |
| 2 | 4.6 | 10 |
| 1 | 2.3 | 4.3 |

This incident power model also allows the equation for temperature rise $\Delta T'$ as the function of spot radius r to be identified as:

$$\Delta T' = (0.0533r^2 + 0.407r)rep\_rate$$

Maximum safe steady-state firing rates for a stationary beam (assuming a maximum temperature rise of 10° C.) may be determined from the following equation:

$$rep\_rate = \frac{\Delta T'}{Constant_{Spotsize}}$$

in which $Constant_{Spotsize}$ is taken from Table 2:

TABLE 2

| MAXIMUM REPETITION RATE STATIONARY BEAM | | |
|---|---|---|
| Spot Diameter | Constant | Rate [Hz] |
| 6 | 1.7 | 6 |
| 5 | 1.35 | 8 |
| 4 | 1.03 | 10 |
| 3 | 0.73 | 14 |
| 2 | 0.46 | 20 |
| 1 | 0.22 | 20 |

FIGS. 14A and 14B graphically illustrates temperature rise for a −10 diopter spherical ablation in which the repetition rate is maintained at a constant 10 Hz (in FIG. 14A), and which a variable repetition rate (VRR) ablation has been performed in which the table has been divided into multiple passes, and in which a variable repetition rate between individual pulses has been assigned according to the principles of the present invention. While the individual pulses (including their sizes and locations) have not changed, the thermal response of the corneal tissue is much more benign when a variable repetition rate is employed, even though the total procedure time has been significantly reduced. FIGS. 14C and 14D similarly illustrate the advantages in thermal response for a procedure involving a −4 diopter spherical correction together with a −4 diopter cylindrical correction.

Figure 15A:
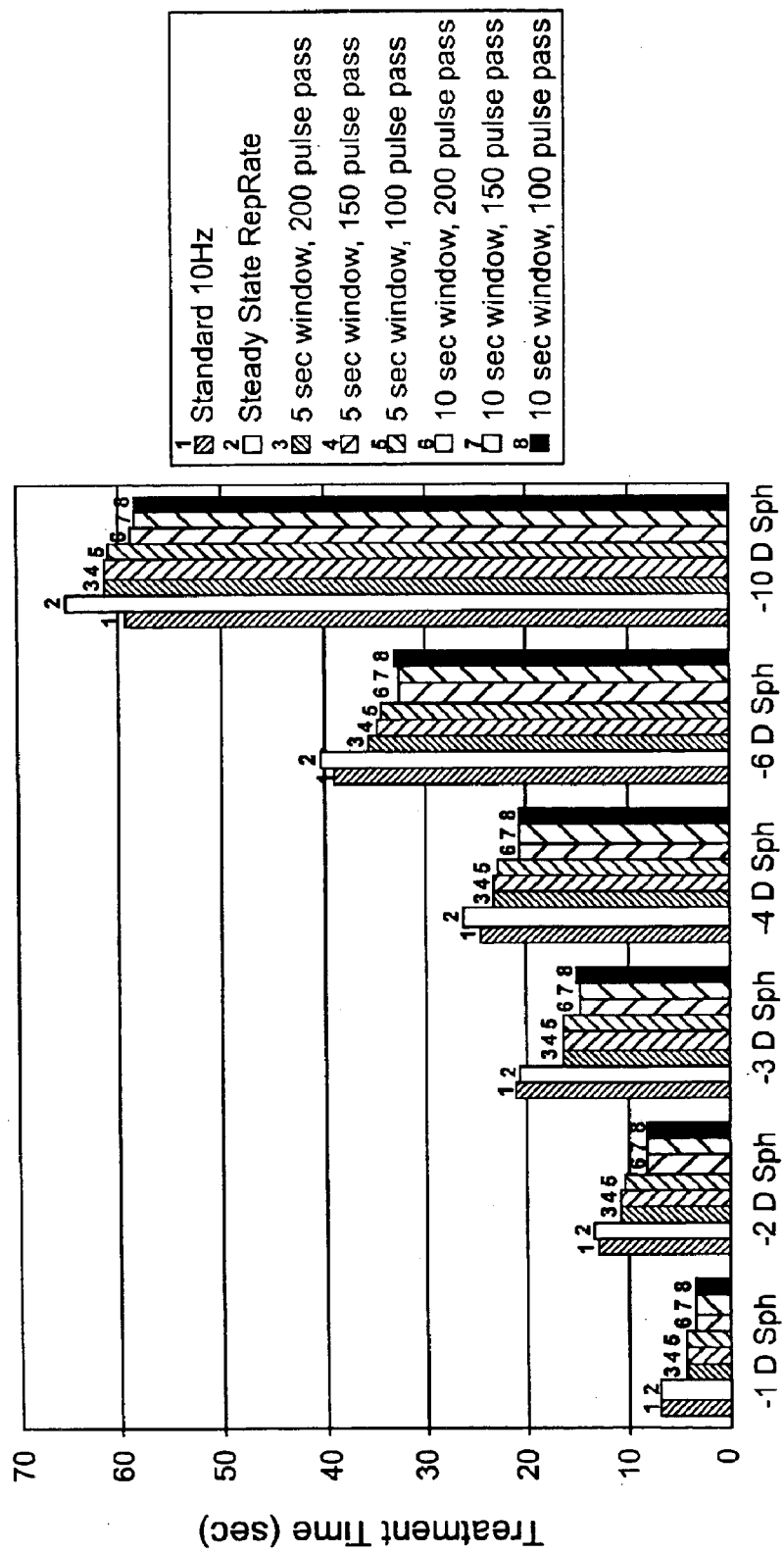
FIGS. 15A–15C graphically illustrate the reduced treatment time provided by the methods and systems of the present invention.
Figure 15B:
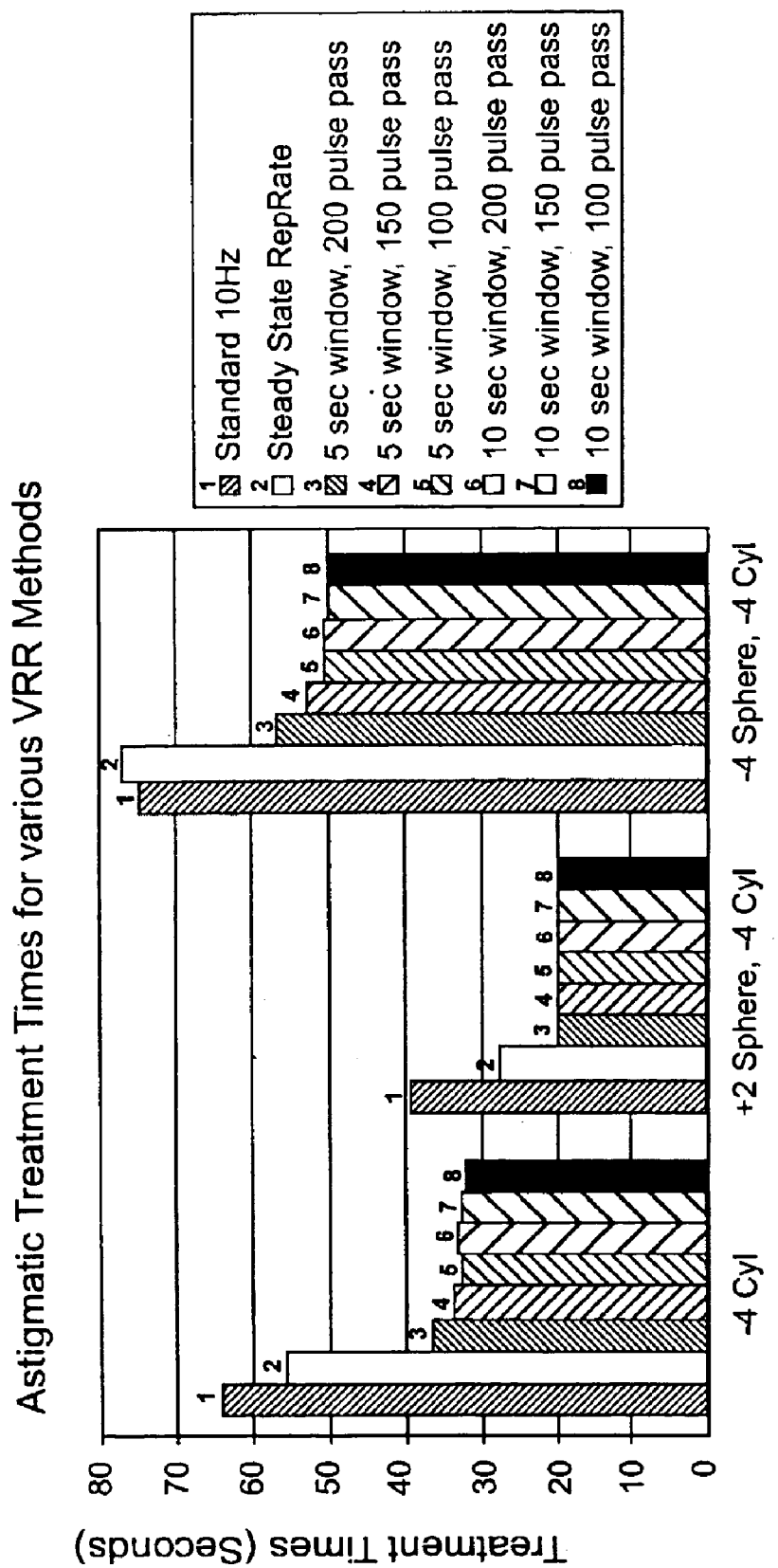
Figure 15C:
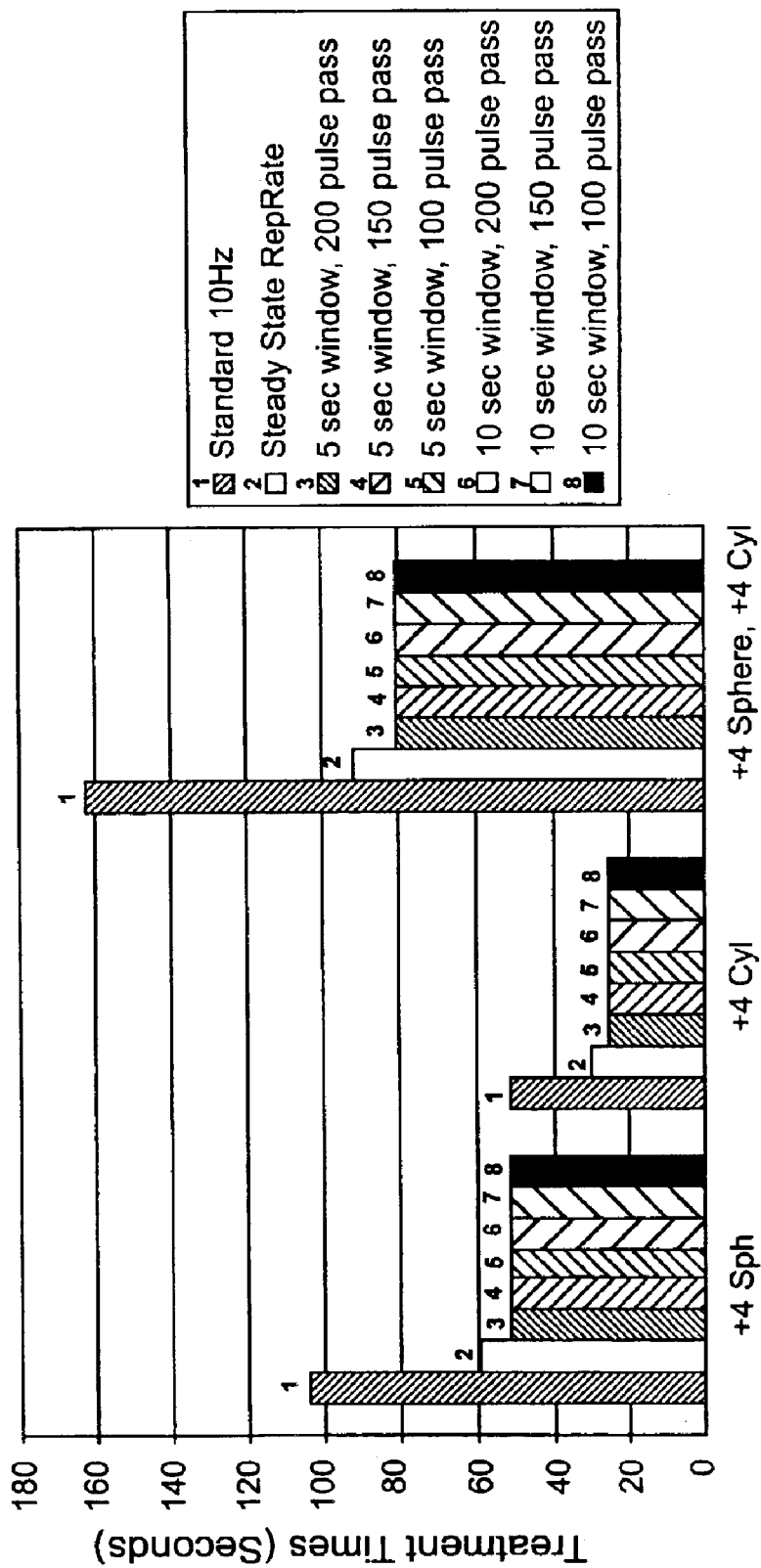

FIGS. 15A through 15C graphically illustrate the reduction in overall ablation procedure treatment times when a variable repetition rate method is employed. While little or no reduction in time may be provided when steady-state repetition rates are employed without time compression, tissue thermal response should benefit. The remaining times illustrate ΔT time windows of 5 and 10 seconds, along with maximum allowable pulses per pass of 200, 150, and 100 for a variety of different myopic treatments (in FIG. 15A), a stigmatic and nixed astigmatic end myopic treatments (in FIG. 15B), and hyperopic treatments (in FIG. 15C).

While the above provides a complete and accurate description of specific embodiments of the invention, several changes and adaptations of the present invention may be readily made. For example, while treatments using several beam diameters have been described, a variable laser firing rate during treatment may be desirable with treatments using only two sizes of a laser beam or only one size of laser beam. Therefore, the scope of the invention is limited solely by the following claims.

What is claimed is:

1. A method for use in planning a corneal refractive procedure, the procedure comprising directing a pattern of ablative laser energy pulses toward a cornea, the method comprising:

determining a safe laser firing repetition rate based on a temperature change limit for the cornea and a relationship between a pulse characteristic and a rise in temperature of the cornea, the pulse characteristic varying according to the pattern.

2. The method of claim 1, wherein the temperature change limit is less than about 12° C.

3. The method of claim 1, wherein the relationship comprises a correlation between change in temperature and at least one of repetition rate and size of the laser beam spot incident on the cornea.

4. The method of claim 3, wherein the relationship indicates a substantially linear relationship between change in the repetition rate and the change in temperature for a given spot size.

5. The method of claim 3, wherein the pulse characteristic comprises the spot size of the laser beam, the relationship indicating a decrease in spot size corresponds with an increase in repetition rate when producing the change in temperature.

6. The method of claim 1, wherein the relationship indicates that a change in temperature $\Delta T$ for a spot size having a radius r and repetition rate rep_rate is:

$$\Delta T = (0.0533 r^2 + 0.407 r) \text{rep}\_{rate}.$$

7. The method of claim 1, further comprising determining a plurality of differing pulse repetition rates defining differing time delays between delivery of sequential pulses of the pattern.

8. The method of claim 7, wherein at least one of the pulse repetition rates comprises an effective pulse repetition rate at a first location over a time period encompassing multiple pulses, the time period being significantly less than a steady-state temperature time, wherein the pulse characteristic comprises locations of the pulses across the cornea, and wherein the effective pulse repetition rate reflects scanning of the laser between the associated first portion of corneal tissue and a second associated portion of corneal tissue during the time period so that the effective pulse repetition rate at the first location over the time period is less than a total firing rate of the laser.

9. The method of claim 7, wherein the temperature change limit comprises an acceptable change in temperature of corneal tissue between a first temperature of the tissue and a maximum desired temperature.

10. The method of claim 9, wherein the first temperature comprises an initial equilibrium temperature of the cornea prior to initiation of the procedure.

11. The method of claim 10, wherein the first temperature is in a range from about 30 to about 35° C.

12. The method of claim 11, wherein the first temperature is about 33° C.

13. The method of claim 10, wherein the first temperature is a measured or estimated temperature of corneal tissue.

14. The method of claim 9, wherein the maximum desired temperature is selected to be less than a hyperthermia temperature of the corneal tissue.

15. The method of claim 9, wherein the maximum desired temperature is less than about 47° C.

16. The method of claim 9, wherein the maximum desired temperature is less than about 44° C.

17. The method of claim 9, wherein the maximum desired temperature is selected based at least in part on a period of time for which corneal tissue will be heated.

18. A method for planning a laser refractive procedure, the procedure comprising directing a pattern of ablative laser energy pulses toward a cornea of the eye, the method comprising:

inputting the pattern in a first order so as to define a first pattern;

deriving a second pattern from the first pattern based on a corneal heating model by at least one of:

i) selectively determining a plurality of differing time delays between sequential pulses, and ii) reordering the pulses of the first pattern; and outputting the second pattern to a laser system for ablating the cornea with the ablative laser energy according to the pattern.

19. The method of claim 18, wherein the time delays are determined by identifying at least one initial thermally safe laser firing repetition rate for the pulses, iteratively reducing the time delays between pulses, and verifying that corneal thermal response remains safe with the reduced time delays.

20. The method of claim 19, wherein the at least one initial repetition rate would result in a safe steady-state corneal tissue temperature if the associated pulses were repeated indefinitely.

21. The method of claim 20, each pulse of the pattern having an associated laser spot size, the spot sizes of the pulses varying according to the pattern, wherein a series of initial thermally safe laser firing repetition rates are identified in response to the spot sizes.

22. The method of claim 19, wherein the corneal thermal response of at least some of the pulses are verified by integrating a plurality of prior pulses within a time window with laser spots encompassing a first location.

23. The method of claim 22, wherein the first location is a central pupil location, and wherein the corneal thermal response of the at least some pulses are also verified at a plurality of outlying locations within a treatment region.

24. The method of claim 22, wherein the pulses within the time window at the first location have different associated spot sizes, wherein the different spot sizes have associated allowable steady state time delays, and wherein the thermal response of the cornea within the time window is verified by combining the allowable time delays for the pulses of different spot sizes to a total time and comparing the total time to the time window.

25. The method of claim 22, wherein the pulses within the time window are scanned across the cornea, wherein the first location is outside at least some of the laser spots of the scanned pulses, and wherein the thermal response is verified using an average pulse rate corresponding to the number of pulses having laser spots encompassing the first location during the time window.

26. The method of claim 18, the pattern comprising a series of laser spot locations across the cornea, wherein the first pattern is assigned a first order, and wherein the deriving step comprises reordering the pattern from the first order to a second order, the pattern of pulses in the second order generating a lower estimated cornea temperature than the pattern in the first order or a lower cornea treatment time than the pattern in the first order.

27. The method of claim 26, wherein the input pattern in the first order defines a first treatment table, wherein the modified pattern in the second order defines a second treatment table, and wherein the laser spot locations and the associated numbers of laser pulses of the first table are the same for the first and second treatment tables.

28. A system for use in planning a corneal refractive procedure, the procedure comprising directing a pattern of ablative laser energy pulses toward a cornea to remove corneal tissue, the system comprising:

- a tangible media embodying machine readable data including the pattern of a tissue-removing ablative laser energy;
- a module having at least one input coupled to the tangible media so as to accept the pattern of tissue-removing ablative laser energy, the pattern including a variable pulse characteristic, the module defining a plurality of differing time delays between sequential pulses of the pattern based on:
- a temperature limit for the cornea; and
- a relationship between the pulse characteristic and a rise in temperature of the cornea.

29. A system for planning a laser refractive procedure, the procedure comprising directing a pattern of ablative laser energy pulses toward a cornea of the eye so as to remove corneal tissue, the system comprising:

- a memory containing the pattern of tissue-removing ablative laser energy as machine readable data;
- a corneal heating model;
- a module assigning a plurality of differing time delays between sequential pulses of the pattern based on the corneal heating model; and
- an output for communicating the time delays for ablation of the cornea.

30. A system for planning a laser refractive procedure, the procedure comprising directing a pattern of ablative laser energy pulses toward a cornea of the eye so as to remove corneal tissue, the system comprising:

- a memory for containing, as machine readable data, the pattern of tissue-removing laser energy in a first order so as to define a first pattern;
- a corneal heating model coupled to the memory;
- a module that derives a second pattern from the first pattern by reordering the pulses of the first pattern based on the corneal heating model.

* * * * *